US011083892B2

(12) United States Patent
Terrando et al.

(10) Patent No.: US 11,083,892 B2
(45) Date of Patent: Aug. 10, 2021

(54) SYSTEMS AND METHODS FOR PERCUTANEOUS NERVE STIMULATION

(71) Applicant: Duke University, Durham, NC (US)

(72) Inventors: Niccolo Terrando, Durham, NC (US); William Huffman, Durham, NC (US); Warren Grill, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 128 days.

(21) Appl. No.: 16/400,698

(22) Filed: May 1, 2019

(65) Prior Publication Data
US 2019/0336770 A1 Nov. 7, 2019

Related U.S. Application Data

(60) Provisional application No. 62/665,661, filed on May 2, 2018.

(51) Int. Cl.
*A61N 1/04* (2006.01)
*A61N 1/36* (2006.01)
*A61N 1/05* (2006.01)

(52) U.S. Cl.
CPC ....... *A61N 1/36053* (2013.01); *A61N 1/0456* (2013.01); *A61N 1/0504* (2013.01); *A61N 1/36021* (2013.01); *A61N 1/36114* (2013.01)

(58) Field of Classification Search
CPC ................ A61N 1/0456; A61N 1/0504; A61N 1/36017; A61N 1/36021; A61N 1/36031; A61N 1/36053; A61N 1/36114
See application file for complete search history.

(56) References Cited

U.S. PATENT DOCUMENTS

| | | | | |
|---|---|---|---|---|
| 2010/0137949 | A1* | 6/2010 | Mazgalev | A61N 1/0587 607/72 |
| 2011/0077660 | A1* | 3/2011 | Janik | A61N 1/0553 606/129 |
| 2011/0093032 | A1* | 4/2011 | Boggs, II | A61N 1/3611 607/42 |
| 2019/0175916 | A1 | 6/2019 | Grill et al. | |

(Continued)

FOREIGN PATENT DOCUMENTS

| | | |
|---|---|---|
| WO | WO 2018/236880 | 12/2018 |
| WO | WO 2019/067446 | 4/2019 |
| WO | WO 2019/118577 | 6/2019 |

OTHER PUBLICATIONS

"Vagus Nerve Stimulation," *AANS* retrieved from https://www.aans.org/Patients/Neurosurgical-Conditions-and-Treatments/Vagus-Nerve-Stimulation on Feb. 4, 2021.
(Continued)

*Primary Examiner* — George Manuel
(74) *Attorney, Agent, or Firm* — Casimir Jones, S.C.; Peter Schlueter

(57) ABSTRACT

The present disclosure provides systems and methods relating to neuromodulation. In particular, the present disclosure provides systems and methods for minimally invasive, targeted, vagus nerve stimulation (pVNS), and the efficacy of this approach with respect to microglial activation and the amelioration of cognitive dysfunction. The systems and methods of neuromodulation disclosed herein can be used to facilitate the treatment of various diseases associated with pathological neural activity.

27 Claims, 14 Drawing Sheets

(56) References Cited

U.S. PATENT DOCUMENTS

2020/0306532 A1 10/2020 Grill et al.
2020/0330767 A1 10/2020 Grill et al.

OTHER PUBLICATIONS

Bergland, Christopher, "Vagus Nerve Stimulation Dramatically Reduces Inflammation," (2016) *Psychology Today* retrieved from https://www.psychologytoday.com/us/blog/the-athletes-way/201607/vagus-nerve-stimulation-dramatically-reduces-inflammation on Feb. 4, 2021.

Shafer and Dean, "Vagus Nerve Stimulation (VNS)," (2018) *Epilepsy* retrieved from https://www.epilepsy.com/learn/treating-seizures-and-epilepsy/devices/vagus-nerve-stimulation-vns on Feb. 4, 2021.

Mayo Clinic Staff, "Vagus nerve stimulation," *Mayo Clinic* retrieved from https://www.mayoclinic.org/tests-procedures/vagus-nerve-stimulation/about/pac-20384565 on Feb. 4, 2021.

Shafer and Sirven, "Epilepsy Statistics," (2013) *Epilepsy* retrieved from https://www.epilepsy.com/learn/about-epilepsy-basics/epilepsy-statistics on Feb. 4, 2021.

"Neurostimulation Devices Market worth over $13 billion by 2023: Global Market Insights, Inc.," (2017) *Global Market Insights, Inc.* retrieved from https://globenewswire.com/news-release/2017/07/12/1042929/0/en/Neurostimluation-Devices-Market-worth-over-13-billion-by-2023-Global-Market-Insights-Inc.html on Feb. 4, 2021.

"Global Vagus Nerve Stimulation Market (2017-2021)—Shift of Surgeons Focus Toward Minimally Invasive VNS Procedures—Research and Markets," (2017) *Business Wire—Research and Markets* retrieved from https://www.businesswire.com/news/home/20170321006367/en/Global-Vagus-Nerve-Stimultion-Market-2017-2021-- on Feb. 4, 2021.

Monk et al., "Predictors of Cognitive Dysfunction after Major Noncardiac Surgery," (2008) *Anesthesiology* 108:1 18-30.

Ogbonnaya and Kaliaperumal, "Vagal nerve stimulator: Evolving trends," (2013) *Journal of Natural Science, Biology and Medicine* 4:1 8-13.

"FDA Releases gammaCore®, The First Non-Invasive Vagus Nerve Stimulation Therapy Applied at the Neck for Acute Treatment of Pain Associated with Episodic Cluster Headache in Adult Patients," (2017) *electroCore* retrieved from https://www.electrocore.com/news/fda-releases-gammacore-the-first-non-invasive-vagus-nerve-stimulation-therapy-applied-at-the-neck-for-acute-treatment-of-pain-associated-with-episodic-cluster-headache-in-adult-patients/ on Feb. 4, 2021.

Huffman et al., "Modulation of neuroinflammation and memory dysfunction using percutaneous vagus nerve stimulation in mice," (2019) *Brain Stimulation* 12 19-29.

\* cited by examiner

SYSTEMS AND METHODS FOR PERCUTANEOUS NERVE STIMULATION

RELATED APPLICATIONS

This application claims priority to and the benefit of U.S. Provisional Patent Application No. 62/665,661 filed May 2, 2018, which is incorporated herein by reference in its entirety for all purposes.

GOVERNMENT FUNDING

This invention was made with Government support under Federal Grant Nos. R01 AG057525 and R21 AG055877-01A1 awarded by the National Institutes of Health. The Federal Government has certain rights to the invention.

FIELD

The present disclosure provides systems and methods relating to neuromodulation. In particular, the present disclosure provides systems and methods for minimally invasive, targeted, vagus nerve stimulation (pVNS), and the efficacy of this approach with respect to microglial activation and the amelioration of cognitive dysfunction. The systems and methods of neuromodulation disclosed herein can be used to facilitate the treatment of various diseases associated with pathological neural activity.

BACKGROUND

Dysregulated immunity is a major hallmark of several disease states and is an attractive target to treat or delay the onset of different conditions, including neurological disorders. Neuroinflammation has been reported to be a critical driver of cognitive deficits, with glia cells playing a central role in this process. Microglia, the resident immune cells of the central nervous system (CNS), continuously surveil the CNS microenvironment and rapidly respond to stimuli, adopting a reactive phenotype characterized by enlarged cell bodies and shortened processes. Although the role of microglial activation and the ensuing morphological changes remains unclear, these alterations are classically associated with pathological features following injury and infection. Lipopolysaccharides (LPS), a key component of the outer membrane of gram-negative bacteria, is widely used to trigger neuroinflammation and ensuing behavioral changes, that are collectively termed "sickness behavior." Systemic endotoxemia induces pro-inflammatory cytokines and profound changes in microglial activity, followed by behavioral dysfunction and, in some cases, neurodegeneration.

The nervous system plays key roles in controlling immunity and fine-tuning responses to inflammatory challenges. The identification of the "inflammatory reflex" provided the first description of a neural circuit capable of relaying information to the brain about the body's inflammatory status and modulating immunity via signaling through the Vagus nerve. Vagal signaling is crucial to the immune-regulatory and pro-resolving effects of this circuit. Recently, electrical vagal nerve stimulation (VNS) has been applied as an alternative therapy in patients with autoimmune disorders to inhibit tumor necrosis factor α (TNF-α), one of the key inflammatory targets in rheumatoid arthritis. The US Food and Drug Administration has evaluated and approved VNS therapy for several conditions, including refractory epilepsy, depression, and migraine, although it remains unclear how parts of these therapeutic effects are mediated.

VNS commonly requires surgical implantation of electrodes around the cervical vagus and has been reported to attenuate systemic inflammation after LPS treatment and to reduce neuroinflammation in rodent models. Although this approach provides direct nerve stimulation, the procedure is invasive and not amenable to acute or ambulatory settings. Noninvasive devices (i.e. transcutaneous VNS) have been developed with promising applications in humans through transauricular and transcervical approaches. However, the specificity of such approaches and their ability to fully engage relevant target nerve fibers remain challenging therapeutic obstacles. Therefore, there is a need for a minimally invasive but effective therapeutic option for vagal nerve stimulation.

SUMMARY

Embodiments of the present disclosure include a percutaneous neuromodulation system. In accordance with these embodiments, the system includes a needle electrode sized and configured for percutaneous placement in proximity to neural tissue in a subject, and a pulse generator coupled to the needle electrode, the pulse generator comprising a power source and a microprocessor, wherein the pulse generator provides to the needle electrode a plurality of charge-balanced pulses to stimulate the neural tissue.

In some embodiments, the neural tissue comprises the vagus nerve. In some embodiments, the neural tissue comprises the vagus nerve and any corresponding afferent or efferent nerve fibers.

In some embodiments, the plurality of charged-balanced pulses are biphasic. In some embodiments, the plurality of charged-balanced pulses are provided at a frequency from about 1 Hz to about 50 Hz. In some embodiments, the plurality of charged-balanced pulses are provided at a frequency from about 5 Hz to about 40 Hz. In some embodiments, the plurality of charged-balanced pulses are provided at a frequency from about 10 Hz to about 30 Hz. In some embodiments, the plurality of charged-balanced pulses are provided for a duration from about 100 µs to about 500 µs. In some embodiments, the plurality of charged-balanced pulses are provided for a duration from about 200 µs to about 400 µs.

In some embodiments, the plurality of charged-balanced pulses are provided at an amplitude sufficient to achieve about a 10% reduction in heart-rate. In some embodiments, the plurality of charged-balanced pulses are provided at an amplitude of about 90% of the minimum amplitude required to produce a 10% reduction in heart rate. In some embodiments, the plurality of charged-balanced pulses are provided for a treatment duration from 1 minute to 1 hour.

In some embodiments, the system further comprises an ultrasound transducer, wherein the ultrasound transducer facilitates the percutaneous placement of the needle electrode in proximity to the neural tissue in the subject.

Embodiments of the present disclosure also include a method for percutaneous neuromodulation using the system described above. In accordance with these embodiments, the method includes programming the pulse generator to output the plurality of charge-balanced pulses, and determining treatment duration, wherein delivery of the plurality of charge-balanced pulses stimulates the neural tissue during the treatment duration and modulates at least one physiological parameter in the subject.

In some embodiments, the at least one physiological parameter comprises reduced inflammation, reduced cytokine production, modulation of microglial activity, and/or reduced memory deficit. In some embodiments, the at least one physiological parameter comprises reduced levels of TNF-α, improved microglial morphology comprising increases in ramified branches, improved episodic memory functioning, and/or improved memory load.

In some embodiments, modulating at least one physiological parameter in the subject comprises modulation with reference to at least one of an untreated subject, the subject prior to treatment, and/or a non-stimulated subject.

Embodiments of the present disclosure also include a method of treating or preventing a neurological disorder. In accordance with these embodiments, the method includes placing a needle electrode in proximity to neural tissue in a subject. In some embodiments, wherein the needle electrode is placed percutaneously, and instructing a pulse generator coupled to the needle electrode to provide to the needle electrode a plurality of charge-balanced pulses to stimulate the neural tissue, wherein stimulating the neural tissue treats or prevents the neurological disorder in the subject.

In some embodiments, treating or preventing the neurological disorder comprises modulating at least one physiological parameter in the subject. In some embodiments, the at least one physiological parameter comprises reduced inflammation, reduced cytokine production, modulation of microglial activity, and/or reduced memory deficits. In some embodiments, the at least one physiological parameter comprises reduced levels of TNF-α, improved microglial morphology comprising increases in ramified branches, improved episodic memory functioning, and/or improved memory load.

In some embodiments, the neurological disorder is at least one of neuroinflammation, postoperative cognitive dysfunction (POCD), epilepsy, depression, migraine, anxiety, neurodegenerative diseases, acute neural injuries, chronic neural disorders, Parkinson's disease, Alzheimer's disease, autism spectrum disorder, delirium disorders, dementia, chemotherapy-induced brain fog, stroke, traumatic brain injury (TBI), or any combination thereof.

In some embodiments, the method further comprises treatment with a therapeutic agent.

In some embodiments, the method is applied according to a treatment regimen. In some embodiments, the treatment regimen comprises one or more stimulation treatments over the course of one day, multiple different days, over the course of weeks, over the course of months, and/or over the course of years. In some embodiments, the treatment regimen comprises a treatment regimen suitable for an acute injury or a treatment regimen suitable for a chronic injury.

BRIEF DESCRIPTION OF THE DRAWINGS

FIG. 1A provides an illustration of one embodiment of the methods of the present disclosure. The animal is in supine position with the ultrasound transducer placed over the shaved cervical region. Anatomical landmarks used in needle positioning include: (a) ventral aspect of cervical region, (b) neck muscles, and (c) carotid artery with blood flow confirmed with Doppler imaging. Needle electrode (d) is visualized and the tip is positioned at the carotid sheath of the vagus for effective nerve stimulation (video images can be provided upon request). FIG. 1B provides representative example of VNS-induced bradycardia. The period of stimulation is denoted with the black bar. Heart rate (HR) is markedly decreased with stimulation (time=0 sec) and quickly recovers (time=15 sec). Bradycardia is defined as a 10% reduction in HR and is plotted as the dashed line (BCT). Stimulation is applied as biphasic pulses at 20 Hz.

FIG. 2A provides a representative schematic image from Allen Mouse Brain Atlas (mouse.brainmap.org) illustrating the NTS and DMX region followed by representative images of c-Fos staining in naïve, sham, and 30 min pVNS mice. Images taken of brainstem region ipsilateral to stimulation after 20 Hz stimulation. Scale bar: 50 μm. FIG. 2B provides representative quantification of c-Fos+ cells in the ipsilateral and contralateral NTS 1 h after pVNS. pVNS significantly induced c-Fos expression in the ipsilateral NTS. FIG. 2C provides representative quantification of c-Fos+ cells in the ipsilateral and contralateral DMX 1 h after pVNS. Bilateral c-Fos+ activation was detected after pVNS in the DMX. FIG. 2D provides representative images of ChAT (left) and c-Fos (middle) in the DMX (scale bar: 50 μm). Double-labeled neurons are visible in yellow (right) in the merged image. FIG. 2E provides representative quantification of ChAT+/c-Fos+ double-labeled cells following pVNS. Bilateral activation was evident in the DMX following 30 min pVNS. Abbreviations: nucleus tractus solitarius (NTS), dorsal motor nucleus of the vagus (DMX), area postrema (AP), central canal (CC), vagus nerve stimulation (VNS), choline acetyltransferase (ChAT). Data are presented as means±SEMs and analyzed by two-way ANOVA and Tukey's post-hoc tests. N=5 mice/group for panels B & C, and N=3 for panel E *P<0.05, P<0.01, *P<0.001, ****P<0.0001 as indicated.

FIG. 3A provides representative results in which preemptive pVNS, 10 or 20 Hz stimulation, significantly reduced LPS-induced TNF-α upregulation at 3 h (n=5-7; *P<0.0001 and P=0.001 respectively). FIG. 3B provides representative results of rescuing effects of pVNS after LPS challenge. 10 Hz pVNS, but not 20 Hz stimulation, was able to reduce plasma TNF-α levels (n=5-7; ***P<0.0001). The data are presented as means±SEMs and analyzed by t-tests. N=5-7 mice/group.

FIG. 4A provides representative images of Iba-1 immunoreactivity in the DG in naïve, LPS (1 mg/kg), 10 and 20 Hz pVNS before LPS administration and representative segmented microglia cells from each of the experimental groups indicating the key morphological features quantified after pVNS and LPS treatments. Scale bars: 50 μm (top panel), 10 μm (bottom panel). FIG. 4B provides representative mean cell counts of ramified compared to non-ramified microglia. LPS induced significant changes in microglia morphology with a shift from ramified to non-ramified cells. Both 10 or 20 Hz pVNS reduced LPS-induced non-ramified microglial morphology. The 10 Hz pVNS restored ramified microglial morphology, but the 20 Hz stimulation was not significant. FIG. 4C provides representative images of Iba1+/CD68+ from the DG region across experimental groups. Scale bar: 10 μm. FIG. 4D provides representative quantification of the percent area of CD68 within Iba1+ cells across experimental groups. The data are presented as means±SEMs and were analyzed by two-way ANOVA and Tukey's post-hoc tests and for CD68% Area, Kruskal-Wallis, followed by Dunn's test. N=3 mice/group, *P<0.05, ****P<0.0001, LPS ramified vs. other ramified groups; ^P<0.05, LPS non-ramified vs. other non-ramified groups.

FIGS. 5A-5C include representative images demonstrating the effects of pVNS on microglial morphology after orthopedic surgery. Reduction in P2RY12 indicates activation of microglia cells (vns sham/surgery), which was restored by pVNS (vns/surgery). FIGS. 5D-5F include representative images pertaining to the evaluation of microgliosis using IBA-1 and P2RY12 after surgery and VNS. Both morphology and density of microglia is reduced after pVNS stimulation.

FIG. 6A provides representative object preference scores for the "What", "Where", and "When" memory task for naïve, 1 mg/kg (i.p.) LPS-t, 10 Hz+LPS-, and 20 Hz+LPS-treated mice. Animals were trained and tested 24 h after treatments. #$P<0.05$, naïve vs other groups; ^$P<0.05$, LPS vs other groups. FIG. 6B provides object exploration times for the novel and now familiar objects in a memory load experiment that sequentially increased the numbers of total objects from 1 to 7 across the 7 consecutive trials. The same mice were used as in the previous episodic memory experiment, except they were tested at 48 h after treatments. The data are presented as means±SEMs and analyzed by RMANOVA followed by Bonferroni corrected post-hoc tests. N=16 mice in the LPS group and 8 mice each in the other three groups. *$P<0.05$, novel vs. other objects in a given trial; #$P<0.05$, naïve vs other groups; ^$P<0.05$, LPS vs other groups; +$P<0.05$, between subjects effects vs. 10 Hz+LPS.

FIG. 7A provides representative results indicating that robust Phospho S6 activation was observed in the brainstem (NTS and DMX) 1 h after 20 Hz pVNS. FIG. 7B provides representative quantification of Phospho S6 in DMX region neurons compared to sham controls. The data are presented as means±SEMs and analyzed by Student's t-test, N=3 mice/group, *$P≤0.05$.

FIG. 8A provides representative microglia images from the naïve and sham controls at the DG region. FIG. 8B provides representative results indicating no significant effects were measured in microglial morphology between naïve and sham pVNS (no stimulation) in hippocampal DG, CA1 and CA3 subregions. FIGS. 8C and 8D provide representative images of CA1 and morphological quantification. FIGS. 8E and 8F provide representative images of CA3 and morphological quantification. Similar protective effects as found in the DG region were observed. The data are presented as means±SEMs and were analyzed by two-way ANOVA and Tukey's post-hoc tests. N=3 mice/group, *$P<0.05$, LPS ramified vs. other ramified groups; ^$P<0.05$, LPS non-ramified vs. other non-ramified groups.

FIG. 9A provides representative schema of the object recognition for "What", "Where" and "When" memory. FIG. 9B provides a representative layout for the memory load task. FIG. 9C provides representative experimental design for behavioral testing. FIG. 9D provides results from the "what-when-where" task of object recognition memory after pVNS. Electrical stimulation improved cognitive domains including the ability to member a previous object (what) and to remember the original location of the displaced object (where) compared to sham controls. This provides demonstrates that pVNS may enhance specific cognitive functions. n=4 mice/group.

FIGS. 10A-10C include representative images demonstrating that glutamate neurotransmission in the hippocampus is regulated by pVNS (vns/surgery).

FIGS. 11A-11B include representative results of mechanical allodynia (FIG. 11A) and cold allodynia (FIG. 11B) after bone fracture in male mice was reduced by pVNS prophylaxis before tibial fracture. Data are presented as Mean±S.E.M. n=5 mice per group. $p<0.05$, Sham vs. 60 min VNS.

DETAILED DESCRIPTION

Figures 1A, 1B:
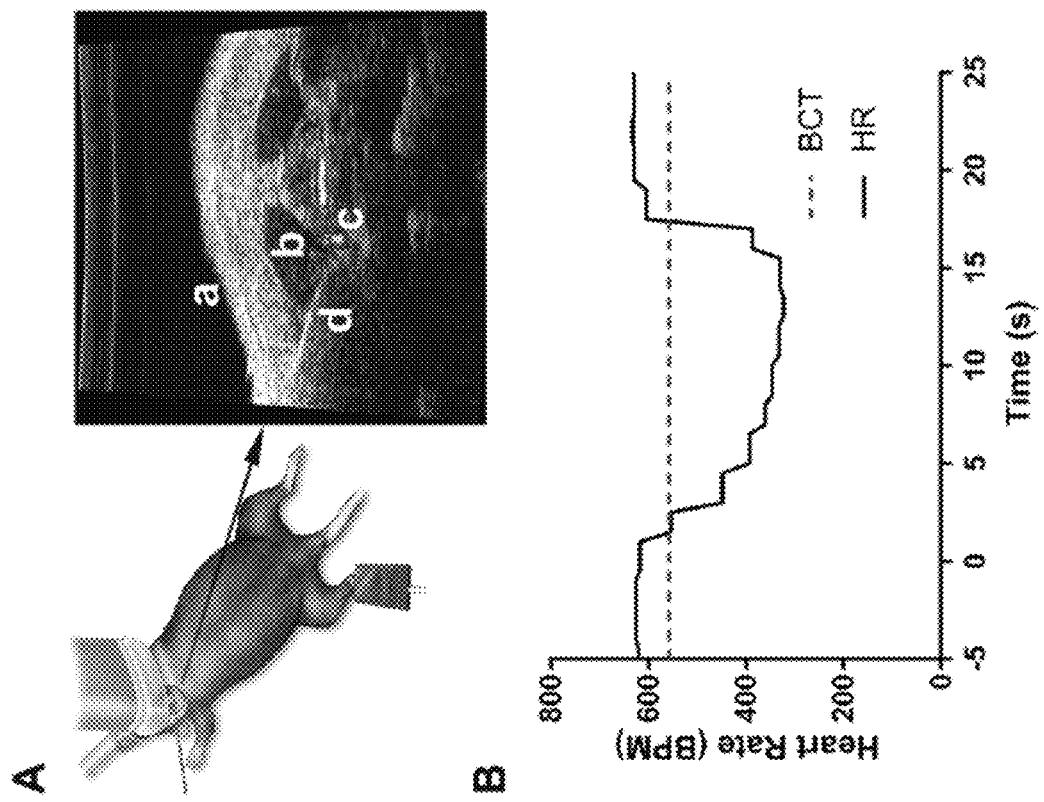
FIGS. 1A-1B: Schematic representation of percutaneous method.

The present disclosure provides systems and methods relating to neuromodulation. In particular, the present disclosure provides systems and methods for minimally invasive, targeted, vagus nerve stimulation (pVNS), and the efficacy of this approach with respect to microglial activation and the amelioration of cognitive dysfunction. The systems and methods of neuromodulation disclosed herein can be used to facilitate the treatment of various diseases associated with pathological neural activity.

Vagal nerve stimulation commonly requires surgical implantation of electrodes around the cervical vagus and has been reported both to attenuate systemic inflammation after LPS treatment and reduce neuroinflammation in rodent models. Although this approach provides direct nerve stimulation, the procedure is invasive and not amenable to acute or ambulatory settings. Non-invasive devices (i.e. transcutaneous VNS) have been developed with promising applications in humans thorough transauricular and transcervical approaches. However, the specificity of these approaches and their ability to engage relevant target nerve fibers remain unclear. To address these limitations, embodiments of the present disclosure provide novel systems and methods involving the selective, percutaneous stimulation of the vagus nerve ("pVNS") using ultrasound-guided needle electrode placement. This approach minimizes surgical manipulations, greatly improves the accuracy of vagal targeting, and can modulate ensuing inflammatory responses. The embodiments provided herein were validated by assessing the vagal-dependent neural circuitry and evaluating the efficacy of this pVNS method in a model of endotoxemia with emphasis on microglia activation and cognitive function.

Embodiments of the present disclosure provide a novel minimally-invasive method to stimulate percutaneously the vagus nerve using ultrasound-guided needle electrode placement. The results provided herein demonstrate that the methods of the present disclosure (generally referred to as pVNS) modulate vagal activity and neuro-immune signaling. Using a robust model of endotoxemia, results of the present disclosure demonstrate the efficacy of this new approach to reduce systemic inflammation, modulate microglial activity in hippocampus, and to restore LPS-induced memory deficits in mice.

The vagus represents a prototypical immunoregulatory reflex circuit with an afferent projection able to sense inflammatory changes and an efferent projection that reduces production of pro-inflammatory cytokines. Using pVNS of the right cervical branch of the vagus nerve, this circuitry was activated, as evidenced by higher c-Fos activity in the ipsilateral than contralateral NTS, where vagal afferent axons terminate. Additionally, bilateral c-Fos activation in the DMX was demonstrated, indicating that pVNS activates fibers in the right cervical vagus which leads to reflex-like activation of efferent fibers in both the ipsilateral and contralateral branches. Heightened activation of ipsilateral DMX neurons may also indicate antidromic activation of efferent fibers directly caused by stimulation.

Systemic inflammation is associated with CNS dysfunction, including neuroinflammation and cognitive impairment. Infection, including edotoxemia, rapidly elevates TNF-α which triggers a cascade of pro-inflammatory cytokines. Embodiments of the present disclosure demonstrate that pVNS reduced systemic levels of TNF-α, a key cytokine that has been extensively studied in different pathologies. Pro-inflammatory cytokines can affect CNS functions and disrupt the blood-brain barrier (BBB). Additionally, pVNS reduced plasma levels of TNF-α both in prevention and rescue paradigms, demonstrating that the systemic anti-inflammatory effects of pVNS may prevent secondary CNS damage and BBB disruption. Thus, VNS methods described herein provide a more localized response and better patient-specific therapeutic outcomes with fewer side effects, especially through the implementation of targeted and minimally invasive approaches.

As described further herein, a robust paradigm with LPS (1 mg/kg) administration was used to induce neuroinflammation and changes in microglial morphology. Following endotoxemia, microglia lose their characteristic ramifications and become hypertrophic. Embodiments of the present disclosure demonstrate that pVNS improved microglial morphology after LPS injection, with more cells retaining ramified branches as found under homeostatic states. In accordance with these embodiments, pVNS reduced microglial activation, including Iba-1 and CD68.

In addition to microglia activation and inflammatory responses, experiments were conducted to investigate whether pVNS could exert any effects on LPS-induced cognitive impairment using a variety of tests. These studies focused upon two separate aspects of cognition—the "what", "where", and "when" of episodic memory and effects on memory load. The "what" memory was unaffected by all treatments. By contrast, "where" and "when" memories were adversely affected by LPS treatment. Both 10 Hz and 20 Hz pVNS prevented the LPS deleterious effects to become manifest during testing for the "where" and "when" tasks and, surprisingly, pVNS boosted performance on these tasks higher than that for the naïve control.

In a further evaluation for cognitive efficacy, mice were subjected to a memory load test. The LPS treated mice were severely debilitated on this task as they were unable to identify the novel object in any of the 7 pairings. The 20 Hz pVNS treatment failed to ameliorate this effect. Unexpectedly, the 10 Hz pVNS treatment group spent more time exploring the novel object when the memory load was increased from 2 or 4 to 7 objects. Moreover, the performance by this group was statistically indistinguishable from that of the sham mice with memory loads of 2, 3, and 6 objects. Thus, the 10 Hz pVNS was highly efficacious and partial rescue was fully evident even with a high memory load of 6 objects.

Taken together, embodiments of the present disclosure demonstrate a novel procedure for stimulating the vagus nerve using a minimally invasive percutaneous needle approach. Treatment with pVNS reduced systemic inflammation, counteracted changes in microglia morphology, and normalized cognitive impairments following endotoxemia. The results described herein demonstrate the therapeutic utility of using bioelectronic approaches to modulate neuro-immune interactions and cognition.

Embodiments of the present disclosure include a percutaneous neuromodulation system. In accordance with these embodiments, the system includes a needle electrode sized and configured for percutaneous placement in proximity to neural tissue in a subject, and a pulse generator coupled to the needle electrode. In some embodiments, the pulse generator includes a power source (e.g., battery) and a microprocessor. The pulse generator is configured to provide a plurality of charge-balanced pulses to the needle electrode in order to stimulate the neural tissue and treat or prevent one or more diseases or disorders. In some embodiments, treating and/or preventing a neurological disease includes altering one or more physiological parameters such that one or more symptoms of the disease is ameliorated or the onset of one or more symptoms of the disease is prevented.

In some embodiments, the neurological systems and methods of the present disclosure can be used to stimulate the vagus nerve, and/or any corresponding afferent or efferent nerve fibers, as described further herein. In some embodiments, stimulating the vagus nerve according to these embodiments treats and/or prevents a neurological condition in a subject. Other neural tissue can be targeted (e.g., neural activity can be stimulated or inhibited) by the systems and methods described herein, as would be readily recognized by one of skill in the art based on the present disclosure.

In some embodiments, the systems and methods of the present disclosure include the application of a plurality of charged-balanced pulses to targeted neural tissue. In some embodiments, the charged-balanced pulses are biphasic. In some embodiments, the plurality of charged-balanced pulses are provided at a frequency from about 1 Hz to about 50 Hz. In some embodiments, the plurality of charged-balanced pulses are provided at a frequency from about 5 Hz to about 40 Hz. In some embodiments, the plurality of charged-balanced pulses are provided at a frequency from about 10 Hz to about 30 Hz. In some embodiments, the plurality of charged-balanced pulses are provided for a duration from about 100 μs to about 500 μs. In some embodiments, the plurality of charged-balanced pulses are provided for a duration from about 200 μs to about 400 μs.

In some embodiments, the plurality of charged-balanced pulses are provided at an amplitude sufficient to achieve about a 10% reduction in heart-rate, which can be determined to be the bradycardia threshold (BCT) in a subject. In some embodiments, the plurality of charged-balanced pulses are provided at an amplitude of about 90% of the minimum amplitude required to produce a 10% reduction in heart rate.

In some embodiments, the plurality of charged-balanced pulses are provided for a treatment duration, which can be pre-determined or can be determined based on one or more physiological parameters of a subject after treatment. In some embodiments, the treatment duration can be from 1 minute to 1 hour, from 5 mins to 1 hour, from 10 mins to 1 hour, from 20 mins to 1 hour, from 30 mins to 1 hour, from 45 mins to 1 hour, from 15 mins to 45 mins, or from 30 mins to 45 mins. In some embodiments, a single treatment (e.g., a single pVNS treatment) can be sufficient to alter one or more physiological parameters such that one or more symptoms of a disease is ameliorated or the onset of one or more symptoms of a disease is prevented.

In some embodiments, the system further comprises an ultrasound transducer. In accordance with these embodiments, the ultrasound transducer facilitates the percutaneous placement of the needle electrode in proximity to the neural tissue in the subject prior to stimulation of, for example, the vagus nerve. Other means for placing the needle electrode percutaneously can also be used, as would be recognized by one of ordinary skill in the art based on the present disclosure.

Embodiments of the present disclosure also include a method for percutaneous neuromodulation using the systems described herein. In accordance with these embodiments, the, method includes programming the pulse generator to output the plurality of charge-balanced pulses, and determining treatment duration, wherein delivery of the plurality of charge-balanced pulses stimulates the neural tissue during the treatment duration and modulates at least one physiological parameter in a subject. The pulse generator is configured to provide a plurality of charge-balanced pulses to the needle electrode in order to stimulate the neural tissue and treat or prevent one or more diseases or disorders. In some embodiments, treating and/or preventing a neurological disease includes altering one or more physiological parameters such that one or more symptoms of the disease is ameliorated or the onset of one or more symptoms of the disease is prevented.

In some embodiments, the subject is a mammal. In some embodiments, the subject is a human. In some embodiments, the method is used to stimulate neural tissue comprising the vagus nerve, and/or any corresponding afferent or efferent nerve fibers, as described further herein. In some embodiments, stimulating the vagus nerve treats and/or prevents a neurological condition in a subject. Other neural tissue can be targeted (e.g., neural activity can be stimulated or inhibited) using these methods, as would be readily recognized by one of skill in the art based on the present disclosure.

In accordance with these embodiments, the methods described herein can be used to modulate at least one physiological parameter that includes, but is not limited to, inflammation, cytokine production, microglial activity, and/or memory deficit. In some embodiments, the at least one physiological parameter includes reduced levels of TNF-α, improved microglial morphology comprising increases in ramified branches, improved episodic memory functioning, and/or improved memory load.

As would be recognized by one of skill in the art, modulating or altering at least one physiological parameter can include increasing or decreasing an aspect of the physiological parameter. In some embodiments, modulating at least one physiological parameter in the subject comprises modulation with reference to at least one of an untreated subject, the subject prior to treatment, and/or a non-stimulated subject.

Embodiments of the present disclosure also include a method of treating or preventing a neurological disorder. In accordance with these embodiments, the method includes placing a needle electrode in proximity to neural tissue in a subject, including placing the needle electrode percutaneously, and instructing a pulse generator coupled to the needle electrode to provide to the needle electrode a plurality of charge-balanced pulses to stimulate the neural tissue. In some embodiments, stimulating the neural tissue treats or prevents the neurological disorder in the subject. The pulse generator is configured to provide a plurality of charge-balanced pulses to the needle electrode in order to stimulate the neural tissue and treat or prevent one or more diseases or disorders. In some embodiments, treating and/or preventing a neurological disease includes altering one or more physiological parameters such that one or more symptoms of the disease is ameliorated or the onset of one or more symptoms of the disease is prevented.

In some embodiments, the subject is a mammal. In some embodiments, the subject is a human. In some embodiments, the method is used to stimulate neural tissue comprising the vagus nerve, and/or any corresponding afferent or efferent nerve fibers, as described further herein. In some embodiments, stimulating the vagus nerve treats and/or prevents a neurological condition in a subject. Other neural tissue can be targeted (e.g., neural activity can be stimulated or inhibited) using these methods, as would be readily recognized by one of skill in the art based on the present disclosure.

In some embodiments, the neurological disorder that is treated and/or prevented includes at least one of neuroinflammation, postoperative cognitive dysfunction (POCD), epilepsy, depression, migraine, anxiety, neurodegenerative diseases, acute neural injuries, chronic neural disorders, Parkinson's disease, Alzheimer's disease, autism spectrum disorder, delirium disorders, dementia, chemotherapy-induced brain fog, stroke, traumatic brain injury (TBI), or any combination thereof.

In some embodiments, the method further includes treatment with a therapeutic agent, including but not limited to, small molecule drugs, biologic drugs, gene therapy agents, antibody-drug conjugates, nucleic acid aptamers, and the like. A method for administering the therapeutic agent is not particularly limited as long as a desired therapeutic effect for a neurological disorder can be obtained. Examples of the method include intravenous administration, oral administration, intramuscular administration, subcutaneous administration, transdermal administration, transnasal administration, and transpulmonary administration. Particularly for a retinal neurological disorder, intravitreal administration can be mentioned. The dosage of the neurological disorder therapeutic agent of the present invention is not particularly limited and can be appropriately adjusted depending upon the physical condition, disease condition, body weight, age and gender of a subject such as a human and an animal. The dosage can be, for example, 0.01 µg to 100 g/kg body weight per day, more preferably 0.1 µg to 10 g/kg body weight per day, and further preferably 1 µg to 1 g/kg body weight per day. The therapeutic agent can be used in combination with other neurological treatments. The administration time period, dosages, and treatment regimens for the therapeutic agent are not particularly limited. For example, the dosage per day can be administered at a single time or several times by dividing the dosage in several portions, prior to or after pVNS treatment.

In some embodiments, the method of the present disclosure is applied according to a treatment regimen. In some embodiments, the treatment regimen comprises one or more stimulation treatments over the course of one day, multiple different days, over the course or weeks, over the course of months, and/or over the course of years. In some embodiments, the treatment regimen comprises a treatment regimen suitable for an acute injury (e.g., traumatic brain injury or stroke) or a treatment regimen suitable for a chronic injury (e.g., Alzheimer's disease). In some embodiments, a single treatment (e.g., a single pVNS treatment) can be sufficient to alter one or more physiological parameters such that one or more symptoms of a disease is ameliorated or the onset of one or more symptoms of a disease is prevented. In other embodiments, multiple treatments are required to achieve the desired alteration of the one or more physiological parameters. A particular treatment regimen can be predetermined, for example, based on a particular disease or disorder, or a particular treatment regimen can be adjusted based on the various physiological parameters associated with a particular subject.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Correlated to" as used herein refers to compared to.

As used herein, the term "percutaneous" refers to penetrating actions that take place through a disruption of the skin, in contrast to "transcutaneous," which refers to penetrating actions that take place through intact skin. For example, the percutaneous placement of a needle electrode involves directly coupling the electrode to target tissue underlying the skin (e.g., nervous tissue) by disruption of the skin tissue itself, whereas transcutaneous placement does not involve disruption of the skin (e.g., at least one part of an electrode is kept outside the intact skin and underlying tissue).

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (e.g., a monkey, such as a cynomolgus or rhesus monkey, chimpanzee, etc.) and a human). In some embodiments, the subject may be a human or a non-human. In one embodiment, the subject is a human. The subject or patient may be undergoing various forms of treatment.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a treatment to a subject that is not at the time of administration afflicted with the disease. "Preventing" also refers to preventing the recurrence of a disease or of one or more symptoms associated with such disease.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, neurobiology, microbiology, genetics, electrical stimulation, neural stimulation, neural modulation, and neural prosthesis described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Methods and Systems

In accordance with the above description, embodiments of the present disclosure include systems for modulating neural tissue in a subject. In some embodiments, the system includes a needle electrode sized and configured for placement in proximity to neural tissue in a subject. In some embodiments, the needle electrode is placed percutaneously such that it lies adjacent to or is in contact with one or more neurons in a subject and is capable of stimulating or inhibiting the activity of the one or more neurons. In some embodiments, the neural tissue comprises the vagus nerve. In some embodiments, the neural tissue comprises the vagus nerve and any corresponding afferent or efferent nerve fibers.

Systems of the present disclosure also include a pulse generator coupled to the needle electrode. In accordance with these embodiments, the pulse generator can include a power source and a microprocessor. In some embodiments, the pulse generator is programmed and configured to provide to the needle electrode a plurality of charge-balanced pulses to stimulate or inhibit the neural tissue. In some embodiments, the plurality of charged-balanced pulses delivered by the pulse generator are biphasic.

The pulse generator can include stimulation generation circuitry, which can include an on-board, programmable microprocessor, which has access to and/or carries embedded code. The code expresses pre-programmed rules or algorithms under which desired electrical stimulation is generated, having desirable electrical stimulation parameters that may also be calculated by the microprocessor, and distributed to the electrode(s) on the lead. According to these programmed rules, the pulse generator can direct the stimulation through the lead to the electrode(s), which serve to selectively stimulate the targeted tissue region. The code may be programmed, altered or selected by a clinician to achieve the particular physiologic response desired. Additionally or alternatively to the microprocessor, stimulation generation circuitry may include discrete electrical components operative to generate electrical stimulation having desirable stimulation parameters. The stimulation parameters can be input to generate a desired plurality of charged-balanced pulses in a given subject, which can include a pulse amplitude; a pulse width (PW) or duration; a frequency of stimulation pulses applied over time; and a shape or waveform of the stimulation pulses. One or more of the parameters may be prescribed or predetermined as associated with a particular treatment regime or indication. In some embodiments, the pulse generator can be programmed to output a stimulation pulse (e.g., on a graphical user interface (GUI)), and the stimulation pulse can represent a pulse having an optimized shape capable of stimulating or inhibiting neural conduction.

In some embodiments, the plurality of charged-balanced pulses are provided at a frequency from about 1 Hz to about 50 Hz. In some embodiments, the plurality of charged-balanced pulses are provided at a frequency from about 2 Hz to about 45 Hz, from about 6 Hz to about 40 Hz, from about 8 Hz to about 35 Hz, from about 10 Hz to about 30 Hz, from about 15 Hz to about 30 Hz, or from about 20 Hz to about 30 Hz. In some embodiments, the plurality of charged-balanced pulses are provided at a frequency from about 5 Hz to about 40 Hz. In some embodiments, the plurality of charged-balanced pulses are provided at a frequency from about 10 Hz to about 30 Hz.

In some embodiments, the plurality of charged-balanced pulses are provided for a duration from about 100 µs to about 500 µs. In some embodiments, the plurality of charged-balanced pulses are provided for a duration from about 150 µs to about 450 µs, from about 200 µs to about 400 µs, or from about 250 µs to about 350 µs.

In some embodiments, the plurality of charged-balanced pulses are provided at an amplitude sufficient to achieve about a 10% reduction in heart-rate. In some embodiments, the plurality of charged-balanced pulses are provided at an amplitude of about 50% of the minimum amplitude required to produce a 10% reduction in heart rate. In some embodiments, the plurality of charged-balanced pulses are provided at an amplitude of about 60% of the minimum amplitude required to produce a 10% reduction in heart rate. In some embodiments, the plurality of charged-balanced pulses are provided at an amplitude of about 70% of the minimum amplitude required to produce a 10% reduction in heart rate. In some embodiments, the plurality of charged-balanced pulses are provided at an amplitude of about 80% of the minimum amplitude required to produce a 10% reduction in heart rate. In some embodiments, the plurality of charged-balanced pulses are provided at an amplitude of about 90% of the minimum amplitude required to produce a 10% reduction in heart rate. In some embodiments, the plurality of charged-balanced pulses are provided at an amplitude of about 95% of the minimum amplitude required to produce a 10% reduction in heart rate. In some embodiments, the plurality of charged-balanced pulses are provided at an amplitude of about 98% of the minimum amplitude required to produce a 10% reduction in heart rate.

In some embodiments, the plurality of charged-balanced pulses are provided for a treatment duration from 1 minute to 5 hours. In some embodiments, the plurality of charged-balanced pulses are provided for a treatment duration from 30 mins to 4 hours, from 45 mins to 3 hours, or from 1 hour to 2 hours. In some embodiments, the plurality of charged-balanced pulses are provided for a treatment duration from 10 mins to 1 hour.

In some embodiments, the system further comprises an ultrasound transducer, wherein the ultrasound transducer facilitates the percutaneous placement of the needle electrode in proximity to the neural tissue in the subject. Other means for visualizing the needle electrode during placement into the subject can also be used, as would be recognized by one of ordinary skill in the art based on the present disclosure.

Embodiments of the present disclosure also include a method for percutaneous neuromodulation using the system described above. In some embodiments, the method includes programming the pulse generator to output the plurality of charge-balanced pulses. In some embodiments, the method includes determining treatment duration, such that delivery of the plurality of charge-balanced pulses stimulates the neural tissue during the treatment duration and modulates at least one physiological parameter in the subject. In accordance with these embodiments, the subject can be a mammal, including a human, and in some embodiments, the neural tissue comprises the vagus nerve and any corresponding afferent or efferent nerve fibers, as described further herein.

In some embodiments, stimulation or inhibition of the neural tissue modulates at least one physiological parameter in the subject, which can include modulating a physiological parameter that treats and/or prevents a disease or condition, or one or more symptoms of a disease or condition. In some embodiments, the at least one physiological parameter comprises reduced inflammation, reduced cytokine production, modulation of microglial activity, and/or reduced memory deficit. In some embodiments, the at least one physiological parameter comprises modulating levels of one or more cytokines (e.g., TNF-α), improved microglial morphology comprising increases in ramified branches, improved episodic memory functioning, and/or improved memory load. In some embodiments, modulating at least one physiological parameter in the subject comprises modulation with reference to at least one of an untreated subject, the subject prior to treatment, and/or a non-stimulated subject.

Embodiments of the present disclosure also include a method of treating or preventing a neurological disorder. In accordance with these embodiments, the method includes percutaneously placing a needle electrode in proximity to neural tissue in a subject. In some embodiments, the method includes instructing a pulse generator coupled to the needle electrode to provide to the needle electrode a plurality of charge-balanced pulses to stimulate the neural tissue, such that stimulating the neural tissue treats or prevents the neurological disorder in the subject. In some embodiments, the neurological disorder is at least one of neuroinflammation, postoperative cognitive dysfunction (POCD), epilepsy, depression, migraine, anxiety, neurodegenerative diseases, acute neural injuries, chronic neural disorders, Parkinson's disease, Alzheimer's disease, autism spectrum disorder, delirium disorders, dementia, chemotherapy-induced brain fog, stroke, traumatic brain injury (TBI), or any combination thereof.

In some embodiments, the method includes treatment with a therapeutic agent before, during, or after neuromodulation, as described above. Therapeutic agents can include agents that alter neurotransmission, modulate neural function, relieve pain, and/or treat or prevent one or more symptoms of a disease or condition. Other therapeutic agents that can be used with neuromodulation systems and methods described herein, as would be recognized by one of ordinary skill in the art based on the present disclosure.

3. Examples

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Effects of Minimally Invasive pVNS on Brainstem Nuclei Activity

Figures 2A, 2B, 2C, 2D, 2E:
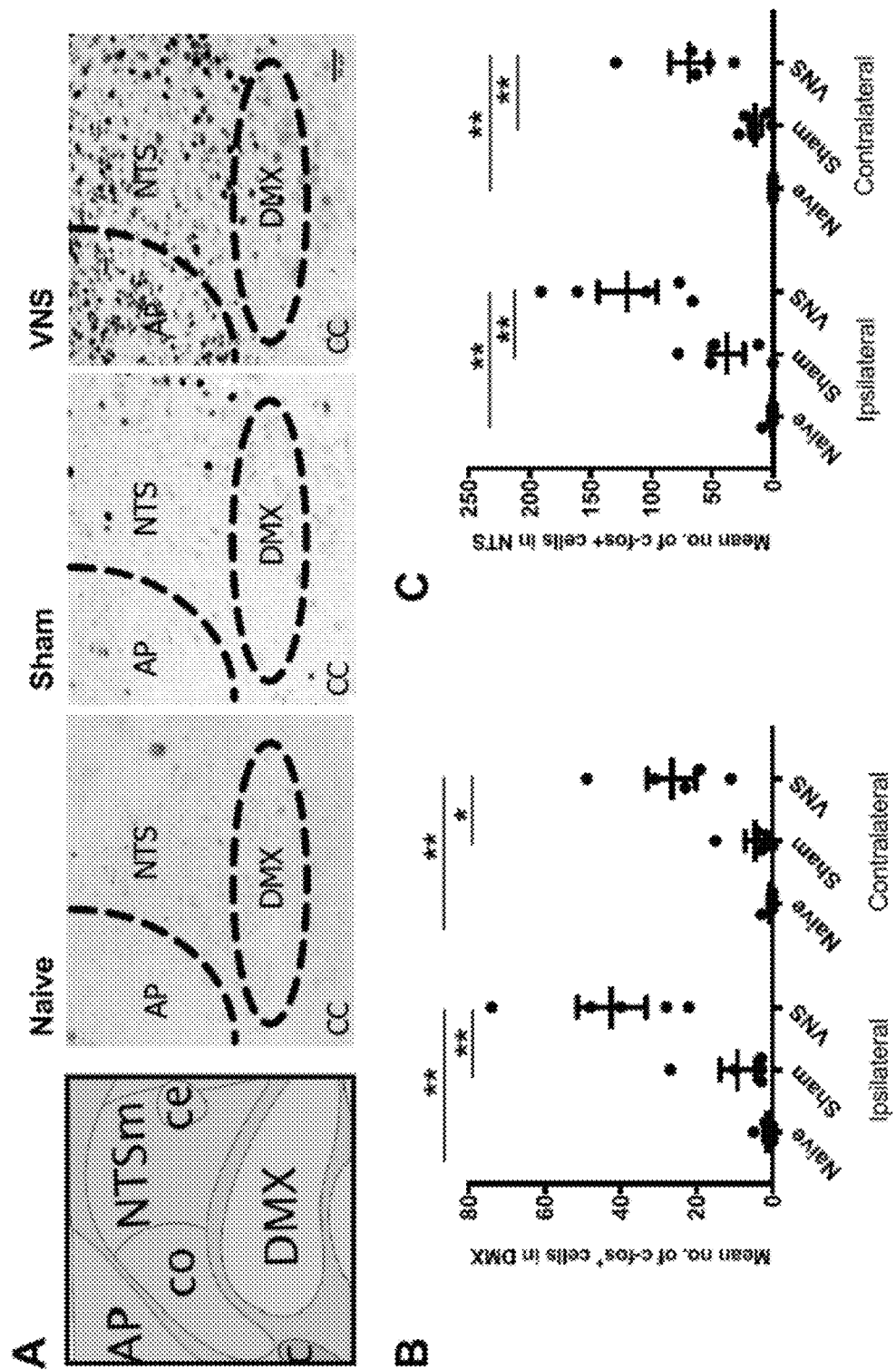
FIGS. 2A-2E: c-Fos and ChAT activation in brainstem nuclei after pVNS.
Figures 2A, 2B, 2C, 2D, 2E:
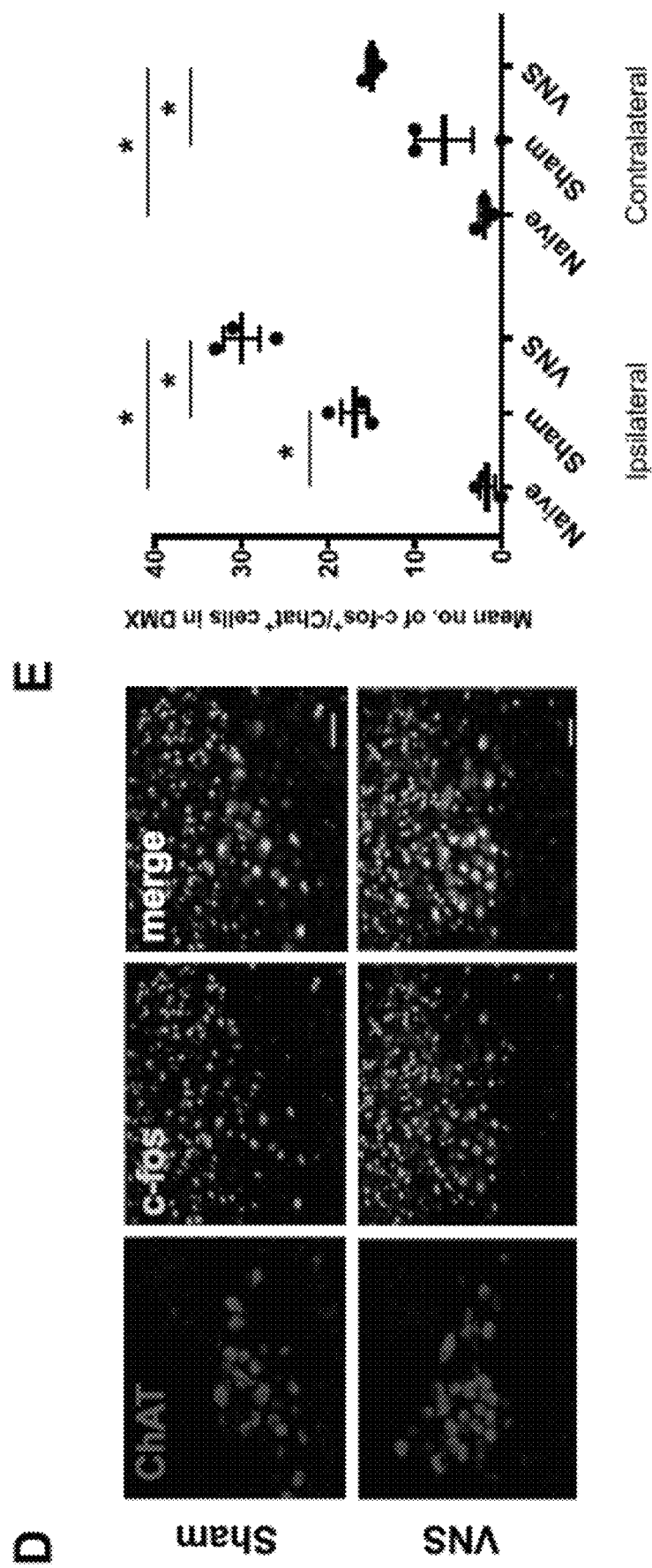
Figures 7A, 7B:
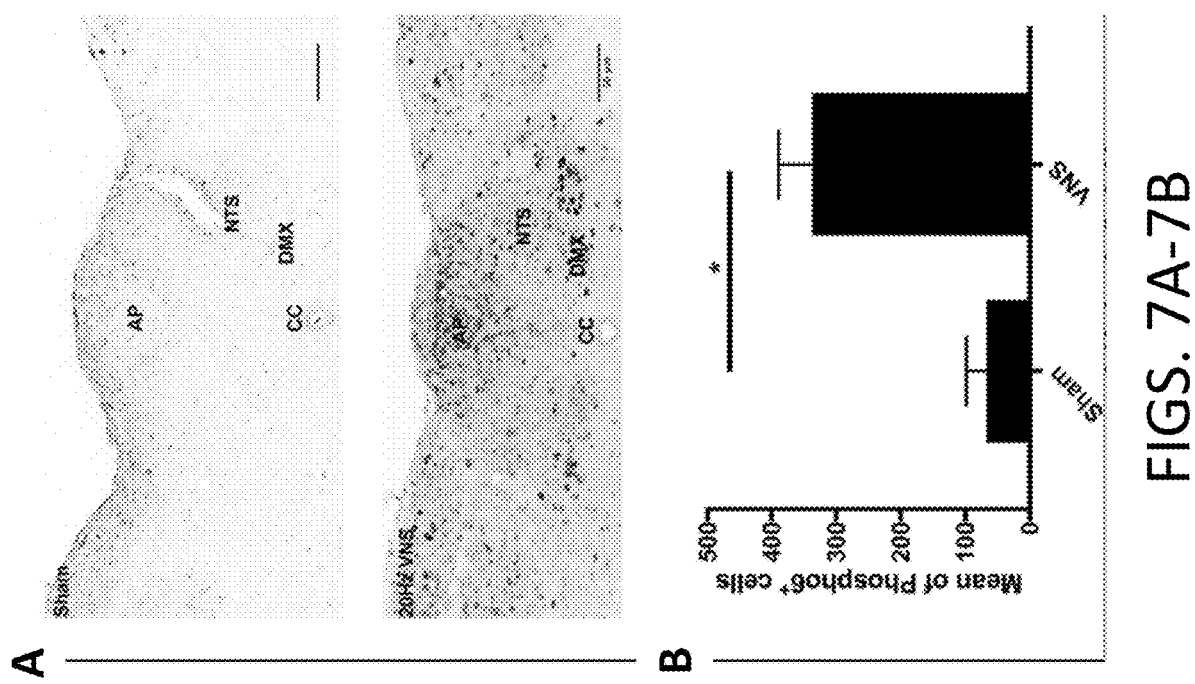
FIGS. 7A-7B: Phospho S6 immunostaining after pVNS.

During ultrasound-guided needle electrode placement, pVNS was delivered to the right vagus nerve while mice were immobile under sevoflurane anesthesia (FIG. 1A). Bradycardia was assessed using non-invasive pulse oximetry to confirm effective stimulation of the vagus in real-time (FIG. 1B). No complications were observed following pVNS; however, one mouse was found dead within 24 h following LPS administration.

c-Fos immunoreactivity was quantified in the NTS 1 h after pVNS to confirm activation of vagal nerve fibers. The pVNS was observed to induce more c-Fos$^+$ immunostained cells in the ipsilateral NTS (120±24; FIGS. 2A-2B) than either in the sham (38±14) electrode placement but no stimulation) [$F(2, 8)=17.36$, $P≤0.01$] or naïve controls (2±2) [$F(2, 8)=17.36$, $P=0.001$]. No significant differences were found between naïve and sham groups. In the contralateral NTS, more c-Fos$^+$ cells were found after pVNS (69±16) compared to sham (15±5) [$F(2, 8)=17.56$, $P≤0.01$] and the naïve group (0±0) [$F(2,8)=17.56$, $P≤0.01$]. Next, efferent fiber activation originating in the DMX was assessed. The number of c-Fos$^+$ immunoreactive cells increased after stimulation both in the ipsilateral (42±9) and contralateral (27±6) DMX as compared to the sham (9±5 ipsilateral, 5±3 contralateral) [$F(2, 8)=17.18$, $P≤0.01$, and $F(2, 8)=12.15$, $P≤0.05$] and naïve control groups (1±1 ipsilateral, 1±1 contralateral) [$F(2, 8)=17.18$, $P≤0.01$, and $F(2,8)=12.15$, $P≤0.01$ respectively] (FIG. 2C). It is noteworthy that there were no differences within groups in the numbers of c-Fos$^+$ cells between the ipsilateral and contralateral DMX nucleus at 1 h. A marker for cholinergic neurons is choline acetyltransferase (ChAT). This enzyme is expressed in the DMX and the effects of pVNS on cholinergic neuronal activity were quantified. The number of c-Fos/ChAT-double positive cells was increased in the DMX (30±2 ipsilateral, 15±1 contralateral) that received pVNS relative to the naïve controls (2±1 ipsilateral, 2±1 contralateral) [$F(2, 12)=66.68$, $P≤0.001$] (FIGS. 2D-2E). The levels of c-Fos/ChAT activation were lower in the contralateral than ipsilateral DMX [$F(2, 12)=9.642$, $P≤0.001$], while significantly more activation was still observed in the pVNS compared to naïve [$F(2, 12)=66.68$, $P≤0.001$], but not sham mice (17±2 ipsilateral, 7±3 contralateral) [$F(2, 12)=66.68$, $P=0.01$]. In addition to c-Fos, ribosomal protein S6 phosphorylation was also assessed as a marker to track neuronal activity. pVNS treatment also resulted in increased levels of Phospho-S6 in the brainstem (337±53) as compared to sham mice (68±31, $P≤0.05$; FIGS. 7A-7B).

Example 2

Validation of pVNS on Systemic Inflammation after Endotoxemia

Figure 3A:
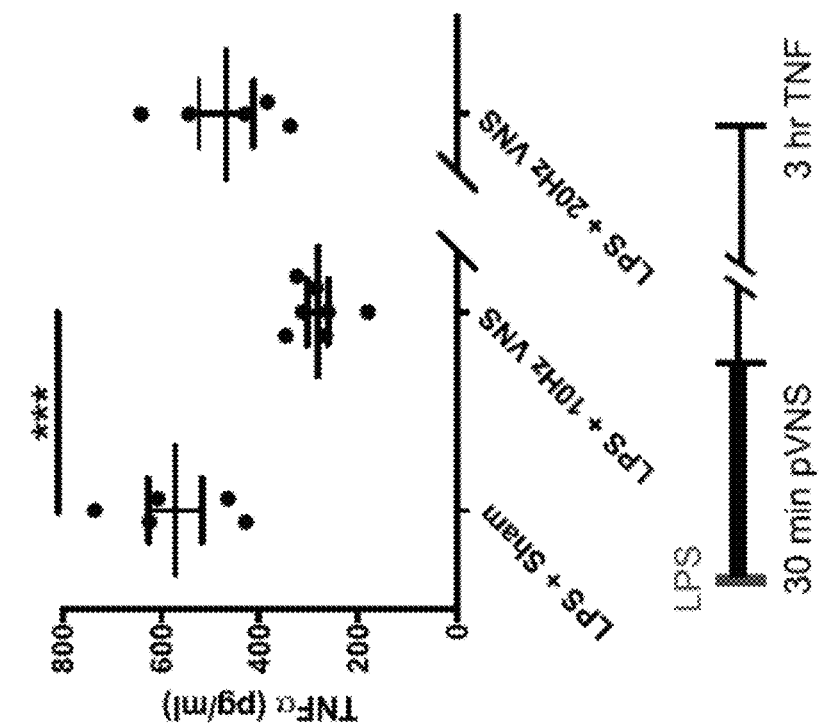
FIGS. 3A-3B: Effects of pVNS on systemic TNF-α induction after endotoxemia.

A robust model of endotoxemia was used to test the efficacy of pVNS to modulate TNF-α, a stereotypical acute pro-inflammatory cytokine that is elevated 3 h after LPS administration, and its levels can be affected by surgical VNS. Anti-inflammatory effects were evaluated using two separate pVNS conditions at 10 Hz or 20 Hz stimulation. In the 10 Hz stimulation paradigm, the amplitude was maintained for 30 min at 100% of the BCT amplitude identified with 20 Hz test stimulation, and did not reduce the HR. In the second paradigm 20 Hz stimulation was maintained for 30 min at 90% of the BCT amplitude identified with 20 Hz test stimulation. LPS induced a robust elevation in plasma TNF-α at 3 h (617±27.68 pg/ml) and this was reduced to similar extents by pre-emptive pVNS at 10 Hz (408.4±20.62 pg/ml, $P≤0.001$) and 20 Hz (460.9±37.45 pg/ml, $P=0.007$; FIG. 3A); no significant differences were observed from the 10 Hz to the 20 Hz conditions.

Figure 3B:
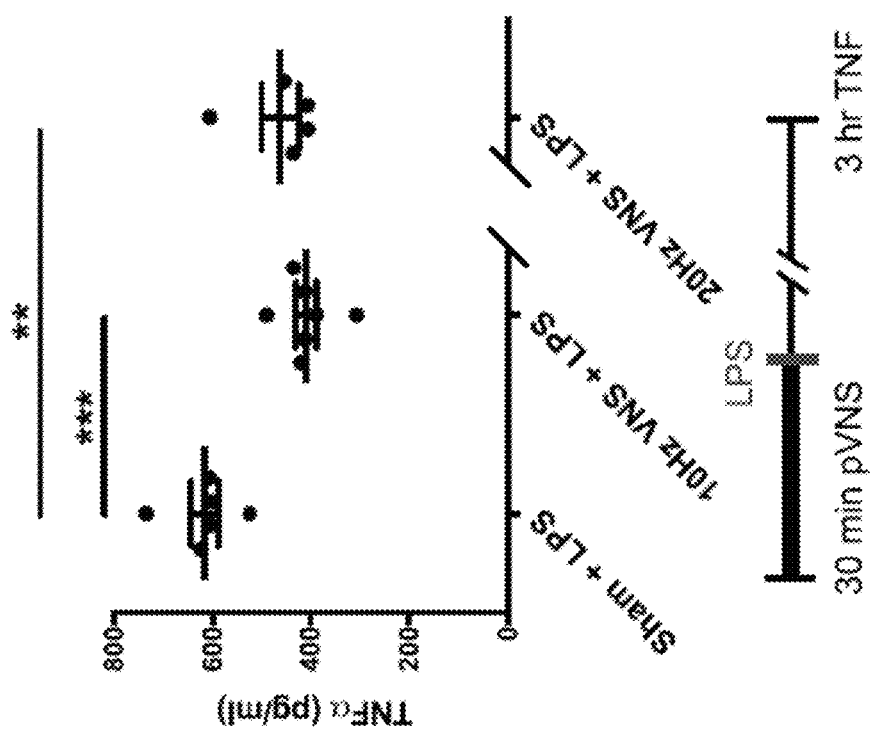

Although in this study LPS was used to mimic a predictable challenge in the immune system, the possible rescue properties of pVNS were also evaluated by injecting LPS prior to stimulation. Notably, 10 Hz stimulation significantly reduced TNF-α levels relative to the sham group (282.5±20.68 pg/ml vs sham LPS group of 571.6±56.31 pg/ml, $P≤0.001$; FIG. 3B) 3 h after LPS treatment (2.5 h. after pVNS). However, no significant effect was observed with the 20 Hz stimulation condition (467.3±55.52 pg/ml, $P=0.200$).

Example 3

Modulation of Microglial Morphology with pVNS

Figures 4A, 4B, 4C, 4D:
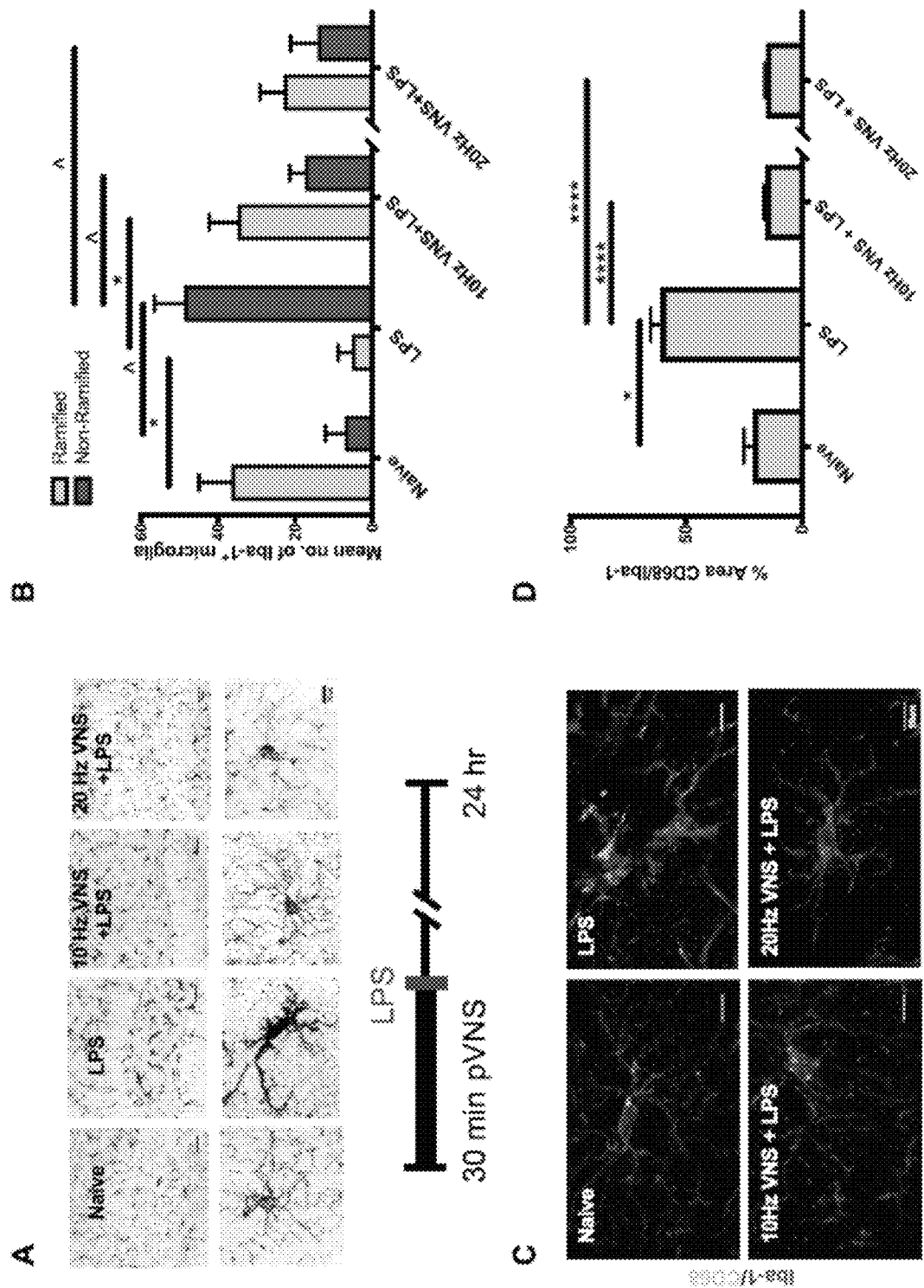
FIGS. 4A-4D: Morphological changes in microglia following pVNS and LPS in hippocampus dentate gyrus region.
Figures 5A, 5B, 5C, 5D, 5E, 5F:
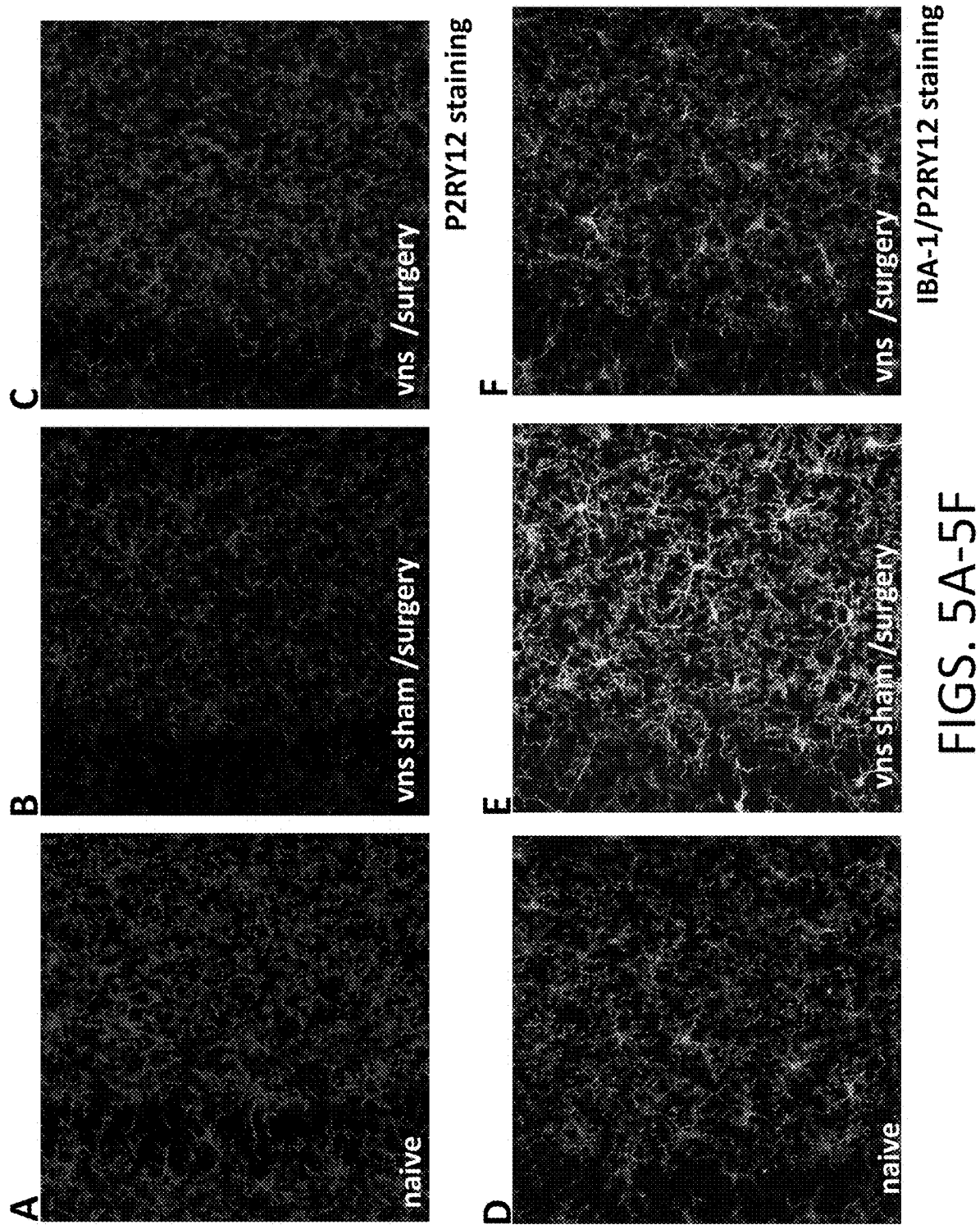
FIGS. 5A-5F.
Figures 8A, 8B, 8C, 8D, 8E, 8F:
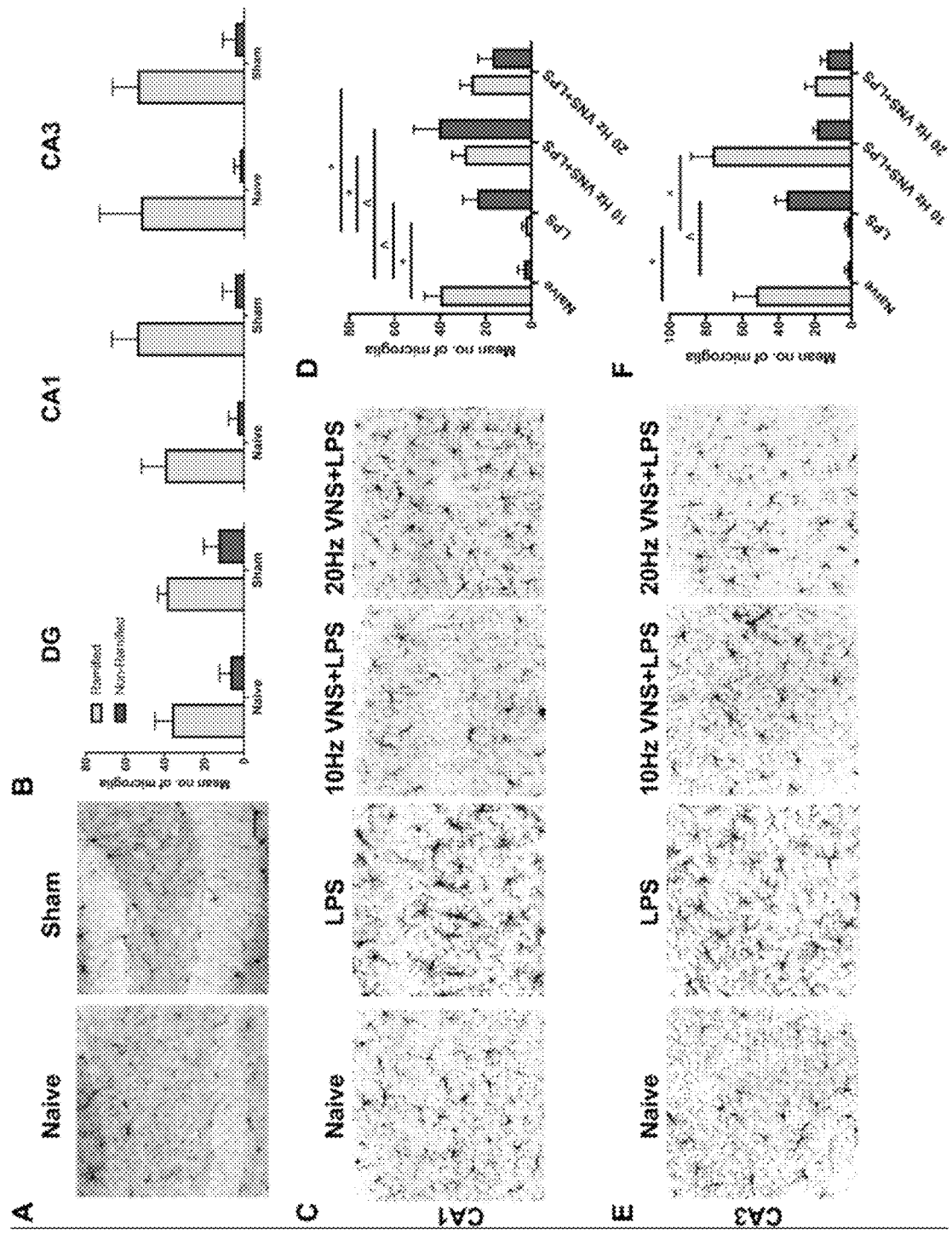
FIGS. 8A-8F: Effects of pVNS on microglia morphology in the CA1, CA3 regions of the hippocampus after LPS.

Neuroinflammation was evaluated by quantifying changes in microglial morphology 24 h after LPS administration and pVNS. Under physiological conditions microglia retain thin and ramified filopodia, critical to their surveillance function. Following challenge, they modify their processes, enlarging their soma and retracting their ramifications, which are associated classically with changes in Iba-1 immunoreactivity. LPS induced morphological changes in microglia, and cells become non-ramified, their soma increased in volume, and there was retraction of their processes (FIG. 4A). Following pVNS at 10 Hz (17±4) or 20 Hz (14±7) fewer non-ramified microglia were observed compared to the LPS group (49±8) [10 Hz: $F(2, 12)=0.3649$, $P=0.010$ and 20 Hz: $F(2, 12)=0.8063$, $P=0.009$]. Interestingly, more ramified cells were observed after 10 Hz pVNS (35±8) relative to LPS-treated mice (5±4, $P=0.010$; FIG. 4B), whereas the 20 Hz pVNS group (23±6) failed to reach significance. Sham pVNS did not induce changes in microglial morphology as compared to naïve controls (36±8 ramified, 7±5 non-ramified; FIGS. 8A-8B). Although these changes were more prominent in the hilus of the DG, similar alterations were observed also in the CA1 and CA3 hippocampus following pVNS treatment (FIGS. 8C-8E). In addition to Iba-1 the area occupied by the lysosomal marker CD68 was also quantified in activated microglia (FIG. 4C). Increased CD68 immunoreactivity was observed 24 h after LPS (60.2±4.9) compared to sham (13.0±1.2, $P≤0.05$) and was significantly reduced by 10 (15.2±1.2) and 20 Hz pVNS (15.1±0.8, $P≤0.0001$ and $P≤0.0001$ respectively; FIG. 4D).

Example 4

Effects of pVNS on Microglial Morphology after Orthopedic Surgery

As shown in FIGS. 5A-5F, neuroinflammation was evaluated in mice 24 h after orthopedic surgery. Postoperative cognitive impairments, including postoperative delirium and longer-lasting postoperative cognitive dysfunction, are significant complications that commonly occur after surgery, critical illness, and hospitalization. Currently, no therapeutics are available to prevent these complications. Neuroinflammation has been described as a putative factor that, upon effective modulation, may alleviate cognitive outcomes in at-risk patients. Using a clinically relevant model of orthopedic surgery, as commonly performed to repair a fracture or replace a joint, postoperative cognitive impairments were investigated. These results demonstrate that pVNS can improve resident microglia activation (marker P2RY12). A reduction in P2RY12 has been associated with activation of these cells (i.e. neuroinflammation). Notably, treatment with 30 min of pVNS (10 Hz) restored the levels of P2RY12 to baseline. Similar rescuing effects were noted when combining P2RY12 with IBA-1; following stimulation activation levels of these markers were more similar to controls than sham treated mice.

Example 5

Rescue of Memory Deficits with pVNS

Figures 6A, 6B:
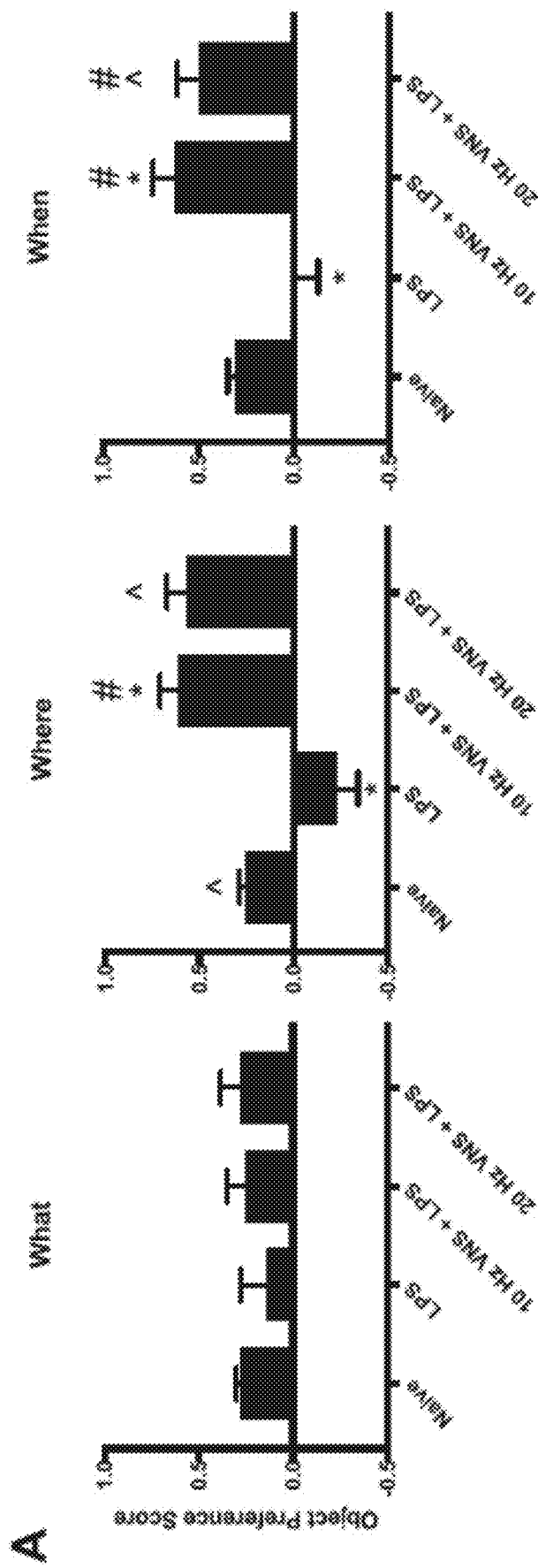
FIGS. 6A-6B: pVNS rescues LPS-induced cognitive deficits.
Figures 6A, 6B:
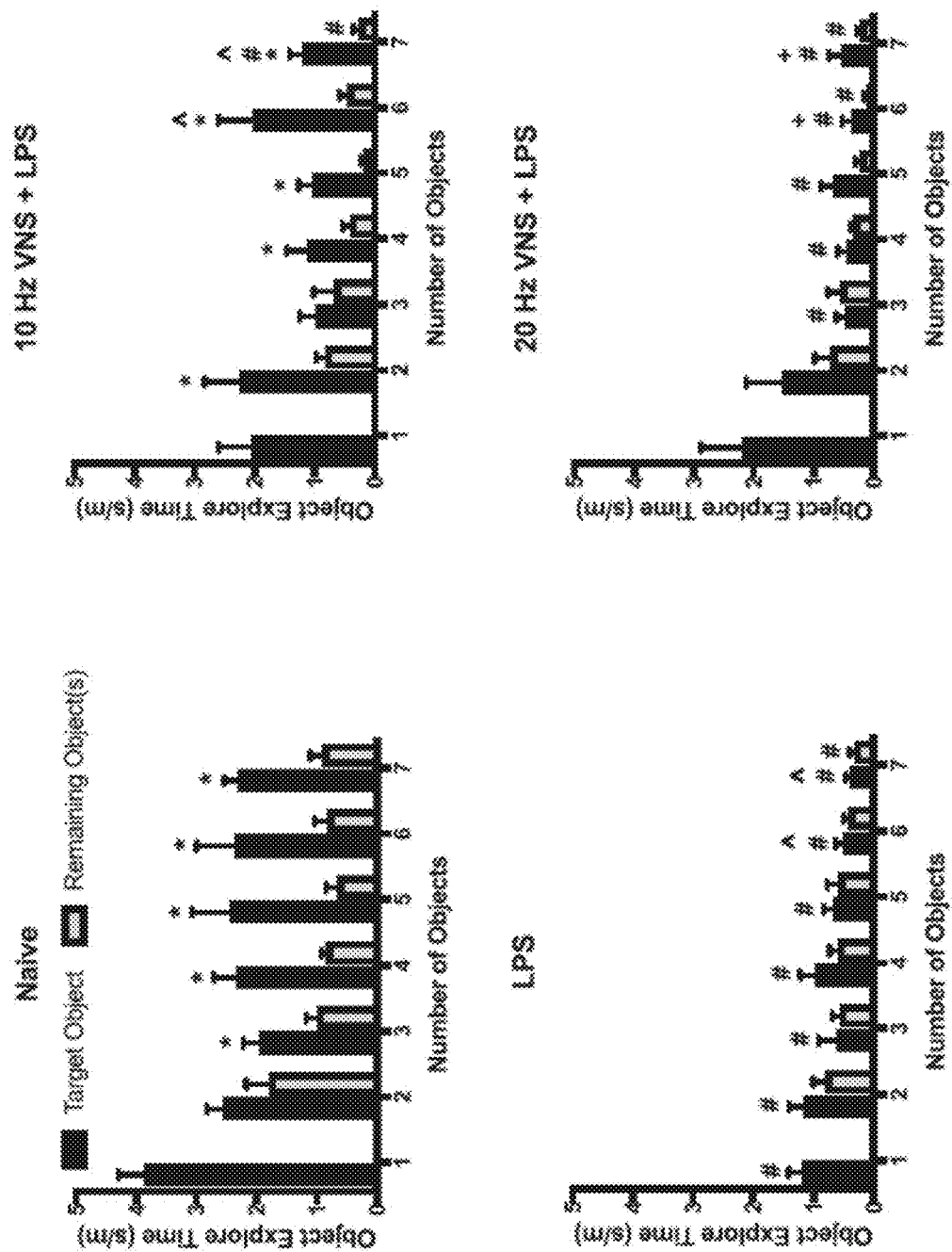
Figures 9A, 9B, 9C, 9D:
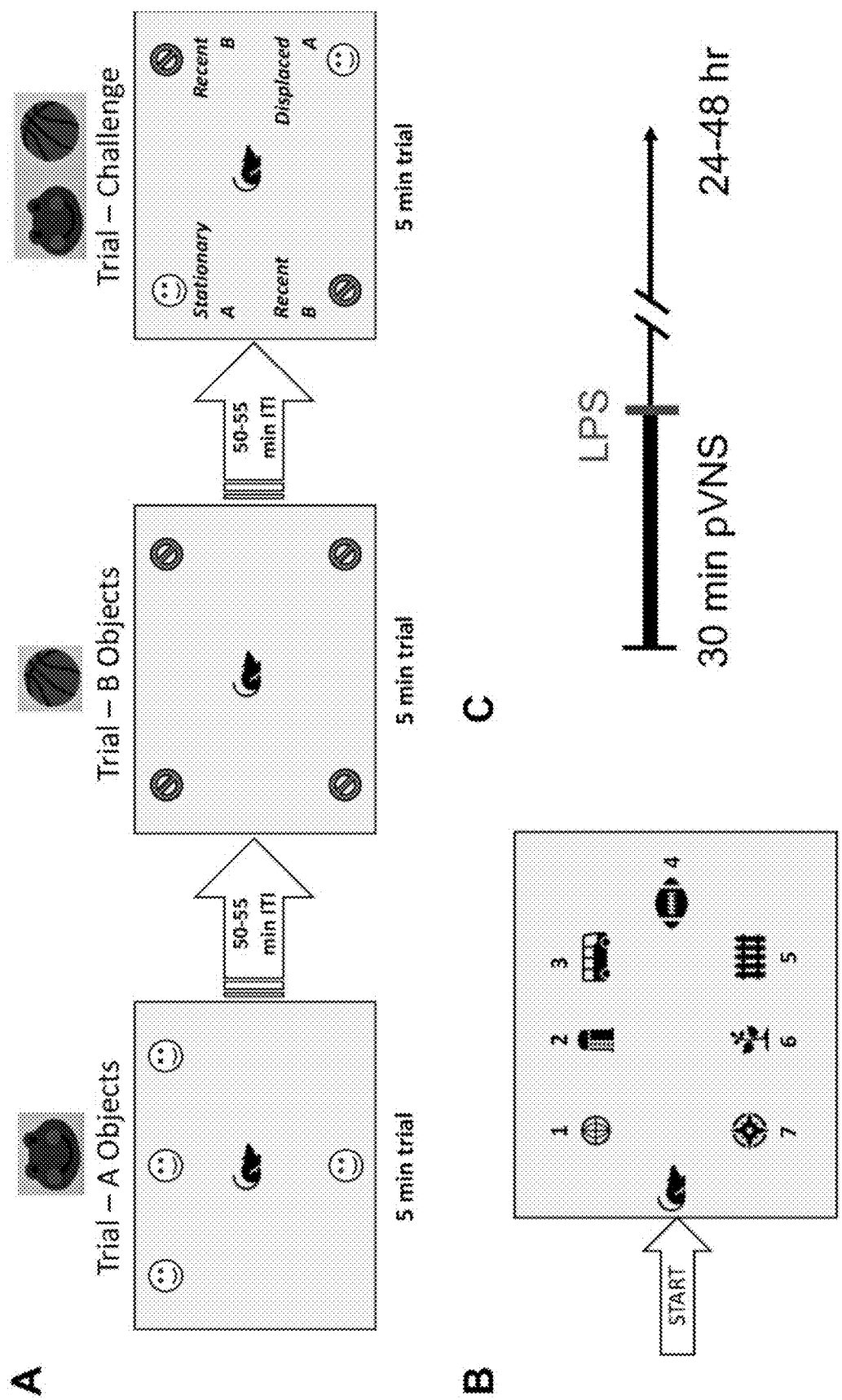
FIGS. 9A-9D.
Figures 9A, 9B, 9C, 9D:
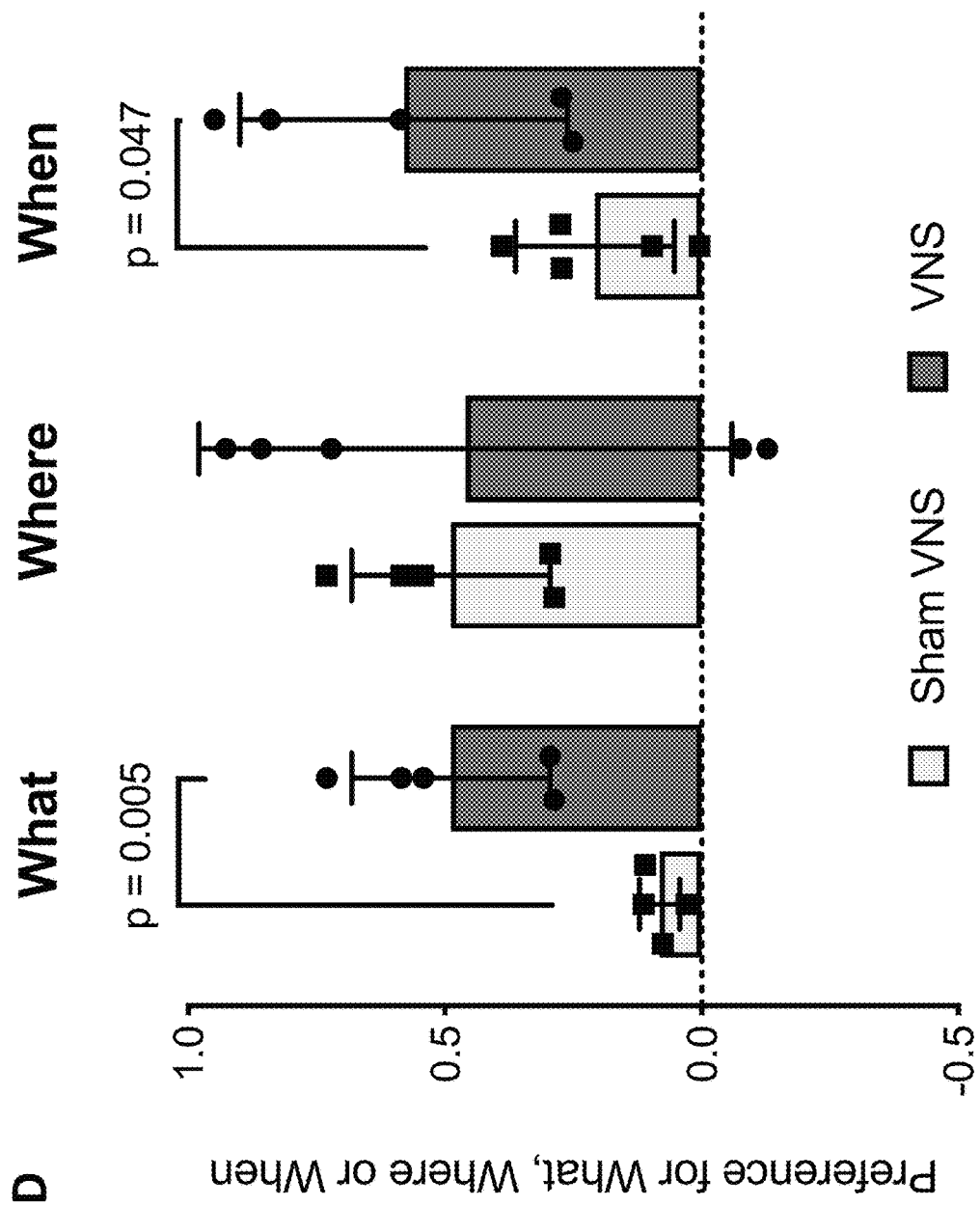

The "What-When-Where" task was used to examine three components of episodic memory; "what" was explored, "where" it was investigated, and "when" it was examined relative to adjacent events (FIGS. 9A-9D). To assess the relationship between neuroinflammation and cognitive functions, the effects of pVNS on its ability to restore cognition were evaluated in LPS-treated mice. The responses of naïve mice, those treated with LPS, and those given 10 Hz or 20 Hz pVNS at the time of LPS administration were examined. While the RMANOVA detected an overall trend among the different memory types $[F(2,60)=1.506, P=0.070]$, the memory-types by treatment interaction was significant $[F(6, 60)=3.213, P=0.008]$ (FIG. 6A). Bonferroni corrected pair-wise comparisons were used to examine the responses within each type of episodic memory. In the "what" memory test, no significant differences were observed among the four groups. In the "when" test, LPS depressed object preference relative to the other three groups ($Ps<0.050$). Interestingly, object preference was enhanced by the 10 ($P<0.042$) and 20 Hz ($P<0.023$) stimulation compared to the naïve group. In the "where" test, a similar relationship was observed where LPS depressed object preference relative to the other groups ($P=0.003$). In this case, only the 10 Hz stimulation enhanced performance over that of the naïve control ($Ps<0.050$). Together, the results indicate that "what" memory is unaffected by LPS or pVNS stimulation, whereby "when" and "where" memories benefited from the pVNS, where the 10 Hz stimulation was particularly efficacious. Means and SEM for "What", "Where" and "When" Test are presented in Table 1.

recognize a novel object when presented with the addition of a new to the already familiar objects over seven trials (FIG. 9B). When exploration times for the novel object became indistinguishable among the other recently experienced objects, the memory load for the task was considered to be exceeded. A RMANOVA for within subject effects found significant main effects for the type of object (novel compared to average of other objects present in trial) $[F(1,36) =127.009, P<0.001]$ and test-trial $[F(6,216)=5.975, P<0.001]$; the object type by treatment $[F(3,36)=15.007, P<0.001]$, object type by trials $[F(6,18)=15.954, P=0.001]$, and the three-way object type by test-trial by treatment $[F(18,216)=1.612, P=0.052]$ interactions were also significant. Bonferroni corrected pair-wise comparisons revealed that within groups, the LPS and the 20 Hz+LPS animals failed to discriminate the novel from the familiar objects across the memory-load trials (FIG. 6B, lower left and right). By striking contrast, naïve mice spent significantly more time exploring the novel than familiar objects when the memory load was increased from 3-7 objects ($P\leq0.003$) (FIG. 6B, upper left). Similarly, the 10 Hz+LPS group spent more time with the novel object when the memory load was augmented with 2 and 4-7 objects ($P\leq0.041$) (FIG. 6B, upper right). Between groups on trial 1, the naïve mice spent more time with the novel object than LPS treated group ($P\leq0.001$), whereas the 10 Hz+LPS and 20 Hz+LPS treatments were not distinguished from the naïve group or those animals given LPS alone.

On trial 2, novel object exploration time was increased in the naïve relative to the LPS mice ($P=0.020$). By trial 3, time with the novel object was enhanced in the sham compared to the LPS and the 20 Hz+LPS groups ($Ps\leq0.033$). The increased memory load on trials 4 and 5 found exploration of the novel object in the sham group to be higher than all other groups ($Ps\leq0.054$). On trial 6, novel object exploration time was augmented in the naïve and 10 Hz+LPS groups relative to the other mice ($P\leq0.051$). Finally, when confronted with 7 objects, the sham mice spent more time with the novel object than all other groups ($P\leq0.003$), while the 10 Hz+LPS group engaged the novel object more than the LPS and 20 Hz+LPS groups ($P\leq0.017$). Together, these findings demonstrate that LPS impairs memory load beginning with the first pair of objects and that 20 Hz pVNS does not improve this condition. In contrast, naïve mice can recognize the novel object even when 7 objects are presented. The 10 Hz pVNS is efficacious in enabling this group to identify the novel object even in trials with as many as 6 familiar objects; however, their overall performance was not always equivalent to that of the naïve controls. Hence, the 10 Hz pVNS is highly efficacious and partial rescue is evident when memory load becomes high. Means and SEM for Memory Load Test are presented in Table 2.

TABLE 1

Means and SEM for "What", "Where" and "When" Test (FIG. 6A)

| Treatment | n | "What" Memory | | "Where" Memory | | "When" Memory | |
| --- | --- | --- | --- | --- | --- | --- | --- |
| | | Mean | SEM | Mean | SEM | Mean | SEM |
| Naïve | 8 | 0.271 | 0.032 | 0.247 | 0.041 | 0.301 | 0.042 |
| LPS | 16 | 0.092 | 0.095 | −0.149 | 0.103 | 0.087 | 0.105 |
| 10 Hz VNS + LPS | 8 | 0.246 | 0.104 | 0.605 | 0.104 | 0.614 | 0.122 |
| 20 Hz VNS + LPS | 8 | 0.275 | 0.106 | 0.565 | 0.107 | 0.488 | 0.122 |

Aside from episodic memory, mice were tested also for memory load. Here, mice were evaluated for their ability to

TABLE 2

Means and SEM for Memory Load Test (FIG. 6B)

| Treatment | n | Number of Objects | Target Object (sec/m) | | Remaining Objects (sec/m) | |
| --- | --- | --- | --- | --- | --- | --- |
| | | | Mean | SEM | Mean | SEM |
| Naïve | 8 | 1 Object | 3.85 | 0.44 | — | — |
| | | 2 Objects | 2.53 | 0.29 | 1.77 | 0.40 |
| | | 3 Objects | 1.92 | 0.29 | 0.98 | 0.19 |
| | | 4 Objects | 2.32 | 0.38 | 0.84 | 0.08 |
| | | 5 Objects | 2.41 | 0.65 | 0.63 | 0.20 |
| | | 6 Objects | 2.34 | 0.65 | 0.79 | 0.23 |
| | | 7 Objects | 2.27 | 0.25 | 0.89 | 0.22 |

TABLE 2-continued

Means and SEM for Memory Load Test (FIG. 6B)

| Treatment | n | Number of Objects | Target Object (sec/m) Mean | SEM | Remaining Objects (sec/m) Mean | SEM |
|---|---|---|---|---|---|---|
| LPS | 16 | 1 Object | 1.16 | 0.25 | — | — |
| | | 2 Objects | 1.14 | 0.26 | 0.78 | 0.21 |
| | | 3 Objects | 0.59 | 0.32 | 0.54 | 0.14 |
| | | 4 Objects | 0.96 | 0.25 | 0.57 | 0.15 |
| | | 5 Objects | 0.66 | 0.16 | 0.58 | 0.19 |
| | | 6 Objects | 0.48 | 0.15 | 0.38 | 0.11 |
| | | 7 Objects | 0.37 | 0.09 | 0.29 | 0.10 |
| 10 Hz VNS + LPS | 8 | 1 Object | 2.04 | 0.55 | — | — |
| | | 2 Objects | 2.23 | 0.60 | 0.81 | 0.16 |
| | | 3 Objects | 0.97 | 0.27 | 0.65 | 0.36 |
| | | 4 Objects | 1.11 | 0.35 | 0.40 | 0.14 |
| | | 5 Objects | 1.02 | 0.24 | 0.16 | 0.06 |
| | | 6 Objects | 2.01 | 0.58 | 0.44 | 0.14 |
| | | 7 Objects | 1.17 | 0.25 | 0.25 | 0.11 |
| 20 Hz VNS + LPS | 8 | 1 Object | 2.15 | 0.72 | — | — |
| | | 2 Objects | 1.51 | 0.60 | 0.69 | 0.28 |
| | | 3 Objects | 0.46 | 0.16 | 0.54 | 0.21 |
| | | 4 Objects | 0.43 | 0.16 | 0.31 | 0.07 |
| | | 5 Objects | 0.66 | 0.21 | 0.21 | 0.09 |
| | | 6 Objects | 0.36 | 0.17 | 0.11 | 0.05 |
| | | 7 Objects | 0.53 | 0.21 | 0.20 | 0.08 |

Example 6

Effects of pVNS on VGluT1 after Orthopedic Surgery

Figures 10A, 10B, 10C:
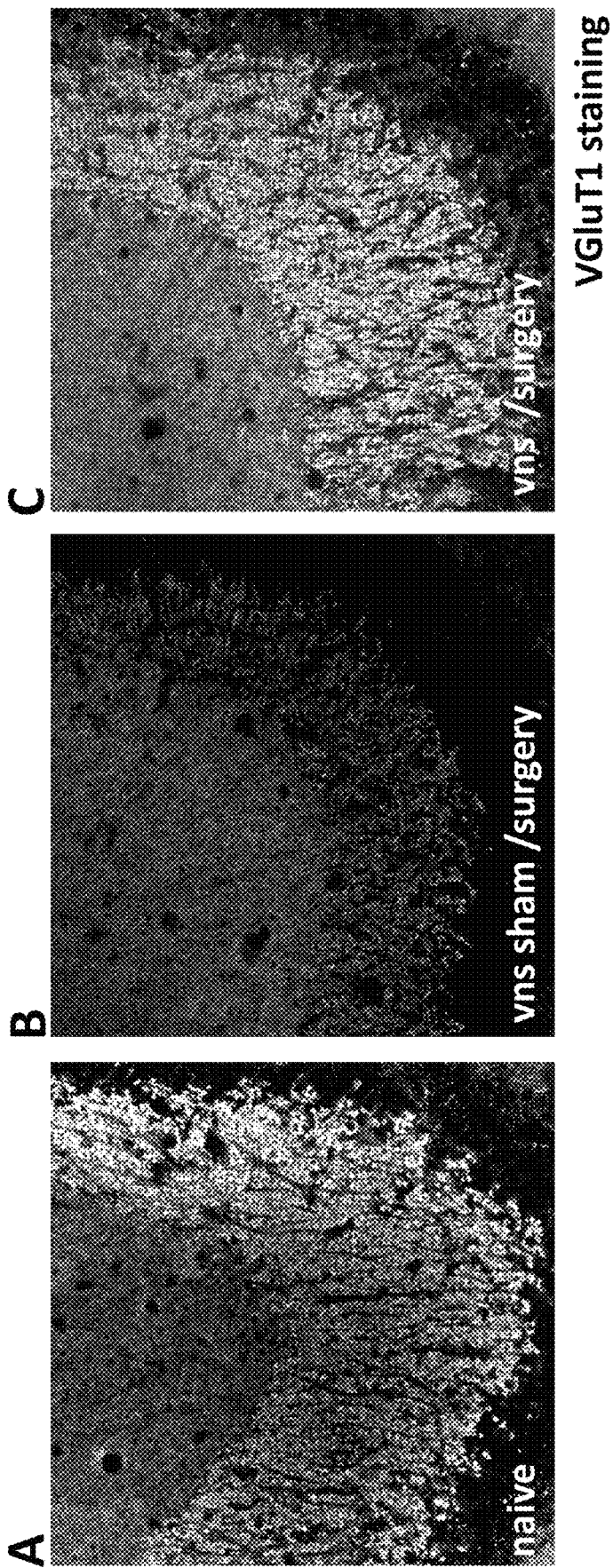
FIGS. 10A-10C: Effects of pVNS on VGluT1 after orthopedic surgery.

VGlut1 is a critical protein involved in synaptic signaling and neurotransmission. Following orthopedic surgery, a significant reduction in the expression levels of VGluT1 was observed in the hippocampus, a key area for memory processing, as shown in FIGS. 10A-10C. Treatment with pVNS (10 Hz, 30 min) was able to restore the surgery-induced deficit in VGluT1, demonstrating that this approach can regulate neuronal activity after surgery.

Example 7 pVNS Reduces Postoperative Pain

Figures 11A, 11B:
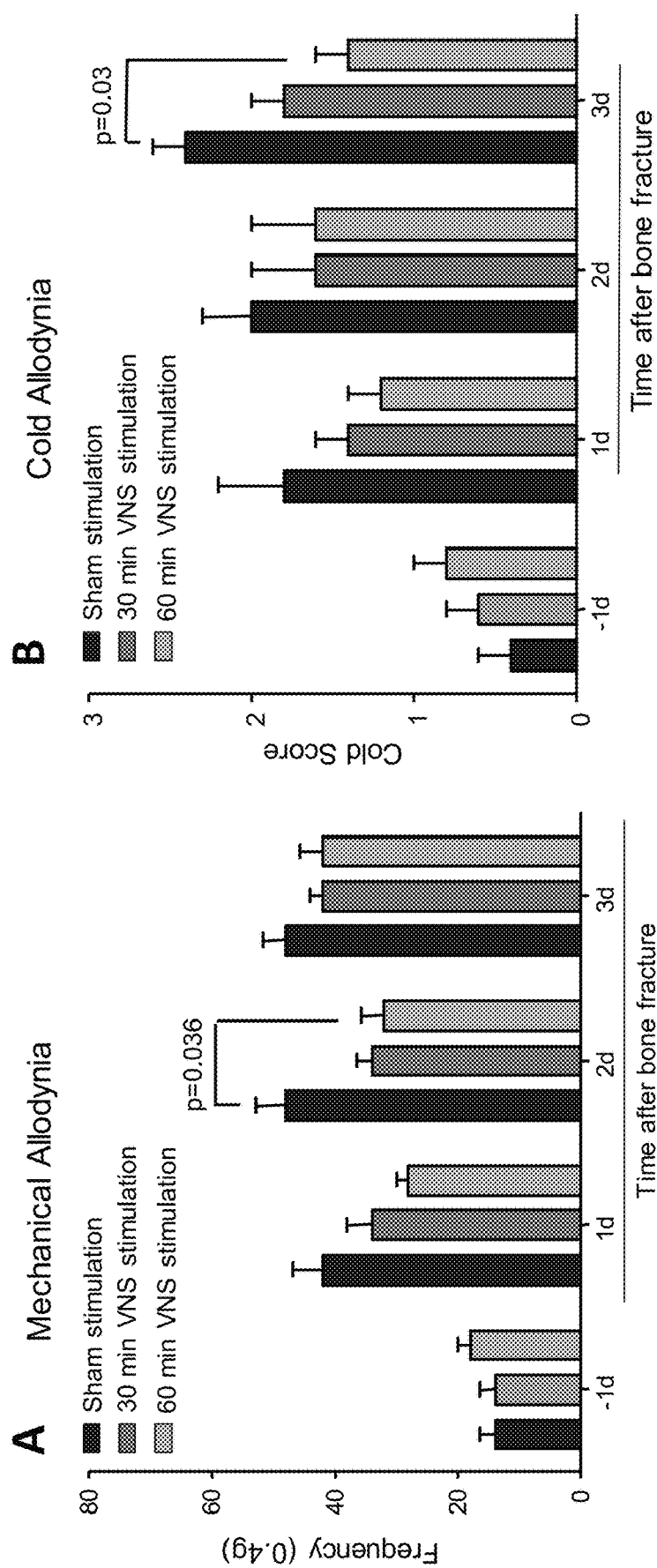
FIGS. 11A-11B: pVNS reduces postoperative pain.

As shown in FIGS. 11A-11B, treatment with pVNS alleviates mechanical allodynia and cold allodynia after bone fracture in male mice. Nerve stimulation was performed before tibial fracture. Data are presented as Mean±S.E.M. n=5 mice per group. p<0.05, Sham vs. 60 min VNS.

4. Materials and Methods

All animal procedures were approved by the Duke University Institutional Animal Care and Use Committee. Inbred male C57BL6/J mice, 12-weeks-old (stock #000664; Jackson Laboratories, Bar Harbor, Me.), were housed 5 mice/cage under environmentally-controlled conditions on a 12 h/12 h light/dark cycle with ad libitum access to food and water. Mice were acclimated for at least 7 days before initiating any procedure. For behavioral testing, mice were transferred to the test rooms 18-24 h before testing and were maintained under the same environmental conditions as described above.

Percutaneous VNS (pVNS).

Mice were anesthetized with 6% sevoflurane (Sevotec Classic T3; SurgiVet, Norwell, Mass.) in an induction chamber and maintained under 3% sevoflurane via a nose-cone delivery system on a heated table. Body temperature was maintained at 37° C. and monitored using a rectal probe. Non-invasive pulse-oximetry was applied to the right paw to monitor heart rate in real-time (MouseSTAT Jr.; Kent Scientific Corporation, Torrington, Conn.). Mice were placed in a supine position and the fur on the ventral aspect of the neck area was removed using hair removal cream (Nair; Church & Dwight, Trenton N.J.). A concentric-bipolar 26 G EMG needle electrode (TECA Elite Disposable Concentric Needle Electrode; Natus Neurology Incorporated, Madison, Wis.) was positioned superficially under the skin in the ventral area over the right cervical branch of the vagus nerve before applying ultrasound gel (Aquasonic 100, Parker Laboratories, Fairfield, N.J.). The ultrasound transducer (VisualSonics Vevo 770 Ultrasound System, Toronto, ON, Canada) was placed in the transverse orientation and positioned to visualize key anatomical landmarks in the neck area, including the carotid artery (by the pulsing movement and identification of blood flow using the Doppler function), trachea, and larynx (FIG. 1A).

The needle electrode was then guided adjacent to the carotid sheath using a micromanipulator. The vagus was electrically stimulated using biphasic, charge-balanced pulses at 20 Hz with 300 μs pulse duration with sufficient amplitude to achieve a 10% reduction in heart-rate (HR), termed the bradycardia threshold (BCT). The vagal stimulation amplitude was reduced to 90% BCT for delivery of 30 min of stimulation (Pulsar 6 bp-as; FHC, Bowdoin, Me.) (video images can be provided upon request). A second stimulation paradigm was used in which that BCT was identified at 20 Hz and, with the amplitude remaining constant, the frequency was decreased to 10 Hz for delivery of 30 min of stimulation. In both stimulation paradigms, bradycardia was induced for a short period (~10 seconds) before either (1) reducing amplitude to 90% BCT for 20 Hz stimulation or (2) reducing frequency to 10 Hz for 10 Hz stimulation, neither of which produced any bradycardic effects during the duration of the stimulation. Electrode placement without stimulation was performed in sham pVNS mice.

Endotoxemia Model.

Lipopolysaccharide (LPS) derived from *Escherichia coli* endotoxin (0111:B4 ultra-pure; InvivoGen, San Diego, Calif.) was dissolved in 0.85% saline and mice were injected intraperitoneally with vehicle (controls) or with 1 mg/kg LPS in a 0.1 ml volume as described. The vehicle or LPS was administered immediately after pVNS. Plasma and brain samples were collected at 3 and 24 h for cytokine expression and microglia activation studies, respectively. A separate cohort of mice underwent behavioral testing.

TNF-α ELISA.

Plasma levels of TNF-α were evaluated at 3 h using a commercially available ELISA kit (BioSource, Camarillo, Calif.) per manufacturer's instructions. Blood was collected via thoracotomy under terminal anesthesia and centrifuged at 2,000 g for 9 min at 4° C., then stored at −80° C. before analysis.

Immunohistochemistry.

Mice were deeply anesthetized with isoflurane and transcardially perfused using 20 ml of 0.1 M PBS (phosphate buffered saline) followed by 30 ml of 4% paraformaldehyde in 0.1 M PBS (pH 7.4). The brains were removed immediately and post-fixed for 3-4 days in 0.1 M PBS with 20% and then 30% sucrose at 4° C. After post-fixation, 50 µm coronal sections from the brainstem region were obtained using a cryostat (Microm HM550; Thermo Scientific, Waltham, Mass.). Sections from naïve, sham, and pVNS treatment groups were processed in parallel. Separate sections were stained for c-Fos (goat anti-c-Fos, sc-52-G; Santa Cruz Biotechnology, Santa Cruz, Calif.), c-Fos/ChAT (rabbit anti-c-Fos, ab190289; Abcam, Cambridge, Mass.; goat anti-ChAT, AB144p; EMD Millipore, Burlington, Mass.) and Phospho-S6 ribosomal protein (Ser235/236) (rabbit anti-pospho S6, #2211; Cell Signaling Technologies, Danvers, Mass.). Sections were blocked with 10% normal donkey serum (D9663; Sigma-Aldrich, St. Louis, Mo.) and incubated for 48 h with primary antiserum.

For single and double c-Fos/ChAT immunostaining, sections were incubated with primary antibodies (1:100) for 48 h at 4° C. On the third day, the sections were washed in PBS and incubated in biotinylated secondary antiserum (against appropriate species IgG, 1:500 in PBS) for 2 h at room temperature (RT). The secondary antibodies used were: donkey anti-goat IgG (H+L) Cross-Adsorbed Secondary Antibody, Alexa Fluor 633; donkey anti-Rabbit IgG (H+L) Highly Cross-Adsorbed Secondary Antibody, Alexa Fluor 488 (all from Invitrogen, Carlsbad, Calif.). For staining of nuclei, DAPI (4',6-Diamidino-2-phenylindole dihydrochloride, 1:1000; Sigma-Aldrich, St. Louis, Mo.) was applied for 20 min in PBS. The sections were mounted, dehydrated and cover-slipped. For negative controls, sections were incubated without the primary antibody to determine whether any non-specific staining was evident. Histology was performed by an investigator blinded to the experimental groups.

c-Fos and Phospho S6 quantification in the nucleus tractus solitarius (NTS) and the dorsal motor nucleus of the vagus nerve (DMX) was performed using 20× and 40× magnified images, respectively and counted bilaterally in 3 sections/brain, with sections taken across the rostral to caudal region of the NTS. Images were captured using a confocal laser scanning microscope (Leica TCS SP8). For counting c-Fos$^+$ and Phospho S6$^+$ cells, a semi-automatic analysis was used that was based upon threshold analysis, using the cell counter plugin of ImageJ software (Version: 1.51w). For quantification of co-localization of c-Fos and ChAT immunolabelling in the DMX, sections were subjected to threshold analysis at 40× magnification followed by a binary process where the signals were masked and merged to reveal the co-localized signal. The co-localized signals were counted using the cell counter plugin of ImageJ software. Counting was performed bilaterally and represented by mean counts per animal by an investigator blinded to the treatment conditions.

For analysis of microglia, the perfusion and staining methods described above were slightly modified. Tissues were post-fixed in 4% PFA for 24 h and sectioned at 75 µm using a vibratome (PELCO easiSlicer; Ted Pella, Inc., Redding, Calif.). Three hippocampal sections/brain were analyzed. Sections were incubated with rabbit anti-Iba1 (1:300; Wako Chemicals, Richmond, Va.) and rat anti-CD68 (1:300; Bio-Rad) for 48 h at 4° C. followed by incubation with secondary antibodies for 2 h in RT. The secondary antibodies used were: donkey anti-rat IgG (H+L) Cross-Adsorbed Secondary Antibody, Alexa Fluor 488 antibody (1:500; Invitrogen) and donkey anti-rabbit Cy3 antibody (1:500; Jackson ImmunoResearch Inc.). Sections were DAPI stained and mounted. For quantification of morphological differences, images were captured at 40× magnification from the dentate gyrus (DG), CA1 and CA3 regions of the hippocampus. A z-stack of 20 µm to 30 µm images was used for quantification from each experimental group.

In each hippocampal subregion, two 40× images were taken. The images were subjected to threshold analysis using ImageJ software. A semi-quantitative analysis was performed by assigning values to microglia based upon the morphology observed. Based upon previously published work, values were assigned to each microglia based on changes in their soma and ramifications (thin soma and long processes vs. enlarged/elongated soma with thick processes) using the cell counter plugin function from ImageJ. The morphology counts for the experimental groups were the mean number of microglia morphologies from the total counts obtained per value (1 or 2) assigned to different morphological states of microglia. For Iba1/CD68 co-localization, z-stack images (63×, zoom 1 of z steps 0.75) were taken. The percent area of CD68 in Iba1$^+$ cells in the DG from 3 mice per group was measured using ImageJ as described in. Histology was performed by an investigator blinded to the experimental groups.

Behavioral Testing.

Mice were behaviorally assessed under two different cognitive paradigms. Twenty-four h after LPS, or combined LPS+pVNS treatments, mice were acclimated for 5 min to a test arena (60×40×24 cm) designed to analyze the "what," "where," and "when" of memory as described. The task was divided into three 5-min phases: exploration of set A objects, exploration of set B objects, and a final test phase with both A and B objects. A 50-55 min inter-trial interval was imposed between each phase. Following acclimatization, mice were exposed to four identical "A" objects presented in a triangular shape (3 objects near the "north" wall and the 4th object near the middle of the "south" wall). In phase 2, mice were presented with four new identical "B" objects arranged in a square (each object near each corner).

In the final phase, mice were tested using a new arrangement of objects. The "B" objects (termed "Recent B") remained in the "northeast" and "southwest" corners of the arena; an "A" object (termed "Stationary A") remained in the "northwest" corner; and a second "A" object (termed "Displaced A) was placed in the "southeast" corner. A video camera was mounted over the test area and was interfaced to a computer equipped with Noldus Ethovision 11.5 (Noldus Information Technology, Asheville, N.C.). Nose-point tracking recorded the duration of contacts with each object (i.e., nose within 2 cm of the object center and body axis of the mouse oriented towards the object). The duration of object investigation was determined for each test phase and preference scores were calculated for the "what", "where", and "when" memories with positive ratios denoting a specific memory and ratios approaching 0 signifying no evidence of this type of memory. "What" memory referred to the mean exploration time for both A objects minus that for the more recent B objects and divided by the total time investigating with both objects. "When" memory represented the difference between object interaction times for the "Stationary A" object and the mean times for both recent "B" objects, divided by the sum of those times. This distinguished old from recent memory. "Where" memory was calculated as the difference between object interaction times for the "Displaced A" object and the "Stationary A" object, divided by the total time with both objects. This metric reflected spatial memory.

Forty-eight h after LPS, or VNS+LPS treatments, memory load abilities were assessed as described. Mice were subjected to seven different test trials, each separated by a 10-15 sec inter-trial interval. In each trial, a new similarly sized object was added successively to the other objects in the arena (42×42×20 cm). For trials 1-3, mice were given 3 min each to explore objects. On trials 4-5 the exploration time was increased to 4 min and on trials 6-7 the mice were given 5 min to explore the objects. Testing began when the mouse was introduced into the arena with the first object. At the end of the trial the mouse was removed. If necessary, the arena was cleaned after mouse removal. The second object was added to the arena and the mouse was reintroduced to the arena.

Mice were always placed initially in the same location relative to the objects. This procedure was repeated until all seven objects were presented. In each trial the newly added object was termed the "target" object. A video camera was mounted over the test arena and nose-point tracking was used as described above. The duration of time spent with the target object and the mean time spent with the remaining objects was calculated from the tracking profiles for each trial. Memory load was determined by the number of trials in which an animal successfully selected the new target object over the previously presented objects. Since memory load was sequentially defined over the consecutive trials, when a mouse no longer preferred the novel object the memory load of the mouse was considered full.

Statistics.

The data are presented as mean±SEM and were analyzed using GraphPad Prism (GraphPad v7.0d; GraphPad Software, San Diego, Calif.) or SPSS 25 software (IBM, Armonk, N.Y.). The data were analyzed by unpaired t-test, 2-WAY ANOVA, or repeated-measures ANOVA. Post-hoc analyses were by Bonferroni corrected pair-wise tests for the behavioral studies or Turkey's multiple comparison tests for the c-Fos analyses and microglial analyses. The CD68 datasets was analyzed by Kruskal-Wallis, followed by Dunn's multiple comparison tests. In all cases, statistical significance was set to $P<0.05$.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

What is claimed is:

1. A percutaneous neuromodulation system comprising:
a needle electrode sized and configured for percutaneous placement in proximity to neural tissue in a subject, wherein the neural tissue comprises the vagus nerve; and
a pulse generator coupled to the needle electrode, the pulse generator comprising a power source and a microprocessor, wherein the pulse generator provides to the needle electrode a plurality of charge-balanced pulses to stimulate the neural tissue, wherein the plurality of charged-balanced pulses are provided at a frequency from about 1 Hz to about 50 Hz.

2. The system of claim 1, wherein the neural tissue comprises the vagus nerve, branches of the vagus nerve, and any corresponding afferent or efferent nerve fibers.

3. The system of claim 1, wherein the plurality of charged-balanced pulses are biphasic.

4. The system of claim 1, wherein the plurality of charged-balanced pulses are provided at a frequency from about 5 Hz to about 40 Hz.

5. The system of claim 1, wherein the plurality of charged-balanced pulses are provided at a frequency from about 10 Hz to about 30 Hz.

6. The system of claim 1, wherein the plurality of charged-balanced pulses are provided for a duration from about 100 µs to about 500 µs.

7. The system of claim 1, wherein the plurality of charged-balanced pulses are provided for a duration from about 200 µs to about 400 µs.

8. The system of claim 1, wherein the plurality of charged-balanced pulses are provided at an amplitude sufficient to achieve about a 10% reduction in heart-rate.

9. The system of claim 1, wherein the plurality of charged-balanced pulses are provided at an amplitude of about 90% of the minimum amplitude required to produce a 10% reduction in heart rate.

10. The system of claim 1, wherein the plurality of charged-balanced pulses are provided for a treatment duration from 1 minute to 1 hour.

11. The system of claim 1, wherein the system further comprises an ultrasound transducer, wherein the ultrasound transducer facilitates the percutaneous placement of the needle electrode in proximity to the neural tissue in the subject.

12. A method for percutaneous neuromodulation using the system of claim 1, the method comprising:
programming the pulse generator to output the plurality of charge-balanced pulses; and
determining treatment duration, wherein delivery of the plurality of charge-balanced pulses stimulates the neural tissue comprising the vagus nerve, branches of the vagus nerve, and any corresponding afferent or efferent nerve fibers, during the treatment duration, and modulates at least one physiological parameter in the subject.

13. The method of claim 12, wherein the subject is a mammal.

14. The method of claim 12, wherein the subject is a human.

15. The method of claim 12, wherein the at least one physiological parameter comprises reduced inflammation, reduced cytokine production, modulation of microglial activity, and/or reduced memory deficit.

16. The method of claim 12, wherein the at least one physiological parameter comprises reduced levels of TNF-60, improved microglial morphology comprising increases in ramified branches, improved episodic memory functioning, and/or improved memory load.

17. The method of claim 12, wherein modulating at least one physiological parameter in the subject comprises modulation with reference to at least one of an untreated subject, the subject prior to treatment, and/or a non-stimulated subject.

18. A method of treating or preventing a neurological disorder, the method comprising:
placing a needle electrode in proximity to neural tissue in a subject, wherein the needle electrode is placed percutaneously, and wherein the neural tissue comprises the vagus nerve, branches of the vagus nerve, and any corresponding afferent or efferent nerve fibers; and
instructing a pulse generator coupled to the needle electrode to provide to the needle electrode a plurality of charge-balanced pulses to stimulate the neural tissue, wherein the plurality of charged-balanced pulses are provided at a frequency from about 1 Hz to about 50 Hz;

wherein stimulating the neural tissue treats or prevents the neurological disorder in the subject.

19. The method of claim 18, wherein the subject is a human.

20. The method of claim 18, wherein treating or preventing the neurological disorder comprises modulating at least one physiological parameter in the subject.

21. The method of claim 20, wherein the at least one physiological parameter comprises reduced inflammation, reduced cytokine production, modulation of microglial activity, and/or reduced memory deficits.

22. The method of claim 20, wherein the at least one physiological parameter comprises reduced levels of TNF-α, improved microglial morphology comprising increases in ramified branches, improved episodic memory functioning, and/or improved memory load.

23. The method of claim 18, wherein the neurological disorder is at least one of neuroinflammation, postoperative cognitive dysfunction (POCD), epilepsy, depression, migraine, anxiety, neurodegenerative diseases, acute neural injuries, chronic neural disorders, Parkinson's disease, Alzheimer's disease, autism spectrum disorder, delirium disorders, dementia, chemotherapy-induced brain fog, stroke, traumatic brain injury (TBI), or any combination thereof.

24. The method of claim 18, wherein the method further comprises treatment with a therapeutic agent.

25. The method of claim 18, wherein the method is applied according to a treatment regimen.

26. The method of claim 25, wherein the treatment regimen comprises one or more stimulation treatments over the course of one day, multiple different days, over the course or weeks, over the course of months, and/or over the course of years.

27. The method of claim 25, wherein the treatment regimen comprises a treatment regimen suitable for an acute injury or a treatment regimen suitable for a chronic injury.

\* \* \* \* \*

UNITED STATES PATENT AND TRADEMARK OFFICE
CERTIFICATE OF CORRECTION

| | |
|---|---|
| PATENT NO. | : 11,083,892 B2 |
| APPLICATION NO. | : 16/400698 |
| DATED | : August 10, 2021 |
| INVENTOR(S) | : Niccolo Terrando, William Huffman and Warren Grill |

It is certified that error appears in the above-identified patent and that said Letters Patent is hereby corrected as shown below:

In the Claims

Claim 16, Column 24, Line 49-50, "TNF-60" should read --TNF-α--.

Signed and Sealed this
Twenty-sixth Day of July, 2022

Katherine Kelly Vidal
*Director of the United States Patent and Trademark Office*